(12) United States Patent
Kanner et al.

(10) Patent No.: US 11,547,555 B2
(45) Date of Patent: *Jan. 10, 2023

(54) INTRAOCULAR LENS DELIVERY DEVICE AND METHOD OF USE

(71) Applicant: Atrion Medical Products, Inc., Arab, AL (US)

(72) Inventors: Rowland W. Kanner, Guntersville, AL (US); Brian A. Roberts, Owens Cross Roads, AL (US); Jonathan David Collins, Arab, AL (US)

(73) Assignee: ATRION MEDICAL PRODUCTS, INC., Arab, AL (US)

( * ) Notice: Subject to any disclaimer, the term of this patent is extended or adjusted under 35 U.S.C. 154(b) by 698 days.

This patent is subject to a terminal disclaimer.

(21) Appl. No.: 16/425,474

(22) Filed: May 29, 2019

(65) Prior Publication Data
US 2019/0274825 A1    Sep. 12, 2019

Related U.S. Application Data

(63) Continuation-in-part of application No. 15/370,647, filed on Dec. 6, 2016, now Pat. No. 10,722,347.

(60) Provisional application No. 62/680,831, filed on Jun. 5, 2018, provisional application No. 62/375,071, filed on Aug. 15, 2016, provisional application No. 62/268,766, filed on Dec. 17, 2015.

(51) Int. Cl.
*A61F 2/16* (2006.01)

(52) U.S. Cl.
CPC ............ *A61F 2/1672* (2013.01); *A61F 2/167* (2013.01); *A61F 2/1667* (2013.01)

(58) Field of Classification Search
CPC ........ A61F 2/16; A61F 2/1662; A61F 2/1667; A61F 2/167; A61F 2/1672
See application file for complete search history.

(56) References Cited

U.S. PATENT DOCUMENTS

| | | | |
|---|---|---|---|
| 4,934,363 A | 6/1990 | Smith et al. |
| 5,190,552 A | 3/1993 | Kelman |
| 5,354,333 A | 10/1994 | Kammann et al. |
| 6,497,708 B1 | 12/2002 | Cumming |
| 6,733,507 B2 | 5/2004 | McNicholas et al. |
| 7,156,854 B2 | 1/2007 | Brown et al. |

(Continued)

FOREIGN PATENT DOCUMENTS

| | | |
|---|---|---|
| EP | 0937443 | 8/1999 |
| EP | 1491163 A2 | 12/2004 |

(Continued)

OTHER PUBLICATIONS

Extended European Search Report that issued in connection with corresponding European application No. 19814614.4 dated Feb. 3, 2022.

*Primary Examiner* — Dianne Dornbusch
(74) *Attorney, Agent, or Firm* — Clark Hill PLC; James R. Foley

(57) ABSTRACT

An IOL delivery device which has a macro movement actuator which is actuateable to move an IOL into position in the device for the IOL to be delivered, and a micro movement actuator comprising at least one pivotable member which is pivotable to deliver the IOL to the eye. The pivotable member may comprise one or more wheels that are rotatable using one's finger.

12 Claims, 18 Drawing Sheets

(56) References Cited

U.S. PATENT DOCUMENTS

| | | |
|---|---|---|
| 8,114,095 B2 | 2/2012 | Rathert |
| 8,246,631 B2 | 8/2012 | Pynson |
| 8,308,736 B2 | 11/2012 | Boukhny et al. |
| 8,721,702 B2 | 5/2014 | Romoda et al. |
| 8,758,433 B2 | 6/2014 | Cole et al. |
| 8,808,308 B2 | 8/2014 | Boukhny et al. |
| 8,998,983 B2 | 4/2015 | Auld |
| 2002/0133116 A1 | 9/2002 | Davis et al. |
| 2004/0147938 A1 | 7/2004 | Dusek et al. |
| 2005/0049606 A1 | 3/2005 | Vaquero et al. |
| 2005/0203542 A1 | 9/2005 | Weber et al. |
| 2006/0167466 A1 | 7/2006 | Dusek |
| 2006/0229633 A1 | 10/2006 | Shepherd |
| 2007/0270881 A1 | 11/2007 | Hishinuma et al. |
| 2008/0086146 A1 | 4/2008 | Ishii et al. |
| 2008/0097459 A1 | 4/2008 | Kammerlander et al. |
| 2008/0255579 A1 | 10/2008 | Wollenhaupt et al. |
| 2009/0204122 A1 | 8/2009 | Ichinohe et al. |
| 2009/0234366 A1 | 9/2009 | Tsai et al. |
| 2009/0270876 A1 | 10/2009 | Hoffmann et al. |
| 2009/0318933 A1 | 12/2009 | Anderson |
| 2010/0106160 A1 | 4/2010 | Tsai |
| 2010/0217273 A1 | 8/2010 | Someya et al. |
| 2010/0228261 A1 | 9/2010 | Feingold et al. |
| 2011/0082463 A1 | 4/2011 | Inoue |
| 2011/0270264 A1 | 11/2011 | Shoji et al. |
| 2012/0022548 A1 | 1/2012 | Zacharias |
| 2012/0283648 A1 | 11/2012 | Veasey et al. |
| 2012/0305441 A1 | 12/2012 | Murray et al. |
| 2012/0310332 A1 | 12/2012 | Murray et al. |
| 2013/0060257 A1 | 3/2013 | Meyer |
| 2013/0197531 A1 | 8/2013 | Boukhny et al. |
| 2013/0226193 A1 | 8/2013 | Kudo et al. |
| 2013/0274756 A1 | 10/2013 | Woods |
| 2014/0200589 A1 | 7/2014 | Anderson |
| 2014/0257315 A1 | 9/2014 | Wu |
| 2014/0257317 A1* | 9/2014 | Safabash ............... A61F 2/1662 606/107 |
| 2014/0276901 A1 | 9/2014 | Auld |
| 2014/0303637 A1 | 10/2014 | Downer et al. |
| 2015/0066044 A1 | 3/2015 | Woods |
| 2015/0088149 A1 | 3/2015 | Auld |
| 2015/0282928 A1 | 10/2015 | Auld et al. |
| 2015/0342726 A1 | 12/2015 | Deacon et al. |
| 2016/0235458 A1 | 8/2016 | Roberts et al. |
| 2016/0287438 A1 | 10/2016 | Badawi et al. |
| 2017/0172727 A1 | 6/2017 | Kanner et al. |

FOREIGN PATENT DOCUMENTS

| | | |
|---|---|---|
| EP | 3210573 A1 | 8/2017 |
| WO | 2011/155636 | 12/2011 |
| WO | 2014/053495 | 4/2014 |
| WO | 2014/129977 | 8/2014 |
| WO | 2016/172113 | 10/2016 |

* cited by examiner

INTRAOCULAR LENS DELIVERY DEVICE AND METHOD OF USE

RELATED APPLICATIONS (PRIORITY CLAIM)

This application is a continuation-in-part of U.S. patent application Ser. No. 15/370,647, now U.S. Pat. No. 10,722,347, filed Dec. 6, 2016, which claims the benefit of U.S. Provisional Application Ser. No. 62/268,766, filed Dec. 17, 2015, and U.S. Provisional Application Ser. No. 62/375,071, filed Aug. 15, 2016, which are hereby incorporated herein by reference in their entirety. This application also claims the benefit of U.S. Provisional Application Ser. No. 62/680,831, filed Jun. 5, 2018, which is hereby incorporated herein by reference in its entirety.

BACKGROUND

The present invention generally relates to an intraocular lens (IOL) delivery device used for inserting an IOL into an aphakic mammalian eye that has undergone, for example, a cataract surgery or into a phakic eye in refractive surgery.

Elimination of an opacified crystal lens through an ultrasonic emulsification and implantation of a lens into an eye that has undergone the elimination of a crystal lens are commonly carried out in cataract surgeries. Currently, a soft IOL (such as is disclosed in United States Patent Application Publication No. 2011/0082463) made of a soft material, such as a silicone elastomer or a soft acrylic material, is used; an optical part of the IOL is folded by an IOL lens folder (such as is disclosed in United States Patent Application Publication No. 2009/0270876) insertion device, the IOL in this state is pushed by a plunger to drive the lens out of a nozzle, and insert it into an eye through an incision made to be smaller than the diameter of the optical part.

IOL insertion devices are designed to insert an IOL into an eye through a tiny incision in order to reduce the possibility of a corneal astigmatism or an infection following surgery. To reduce the possibility of a corneal astigmatism or an infection following surgery, it is desirable to minimize the incision used for inserting an IOL into an eye as much as possible. This requirement in turn places additional demands upon the IOL delivery device.

In order to further reduce the size of the incision, it is necessary to fold an IOL into a smaller size to accommodate the miniaturization of the incision. Folding an IOL into a smaller size while attempting to push it through the necessarily small folder increases friction between the lens and folder thereby resulting in increased resistance to advancement of the plunger used to push a lens out of the IOL delivery device and into an eye. The IOL delivery device plunger must therefore be driven with great force, but in a very controlled manner and without a quick surge of stored energy upon release of the IOL into the eye as it exits the folder's delivery tube.

Syringe like, manually driven delivery devices are hard for users to control, particularly when the IOL exits the folder's tube and the large force necessary for delivery drops almost immediately to zero. Upon this transition of force, there exists a real possibility for the user to lose control of the device tip inserted within the miniature incision and cause tearing or injury to the eye. Similarly, manually operated screw based IOL delivery devices tend to deliver lenses very slowly; they can require two hands to operate, and the user motion necessary to operate them results in moving, pulling and pushing of the IOL folder's tube against the miniature incision which again risks tearing the tissue.

Many surgeons prefer to have one hand free to help steady the patient's eye during lens implantation. Electrically driven (i.e., U.S. Pat. Nos. 5,354,333; 8,308,736 and 8,808,308), hydraulically controlled (i.e., United States Patent Application Publication No. 2008/0255579 and European Patent No. EP 0937443), high pressure gas driven (i.e., U.S. Pat. No. 8,998,983 and United States Patent Application Publication No. 2015/0282928) and spring driven (European Patent No. 0937443 and United States Patent Application Publication No. 2015/0088149) types of delivery mechanisms have been contemplated and/or introduced into the marketplace. While these forms of delivery devices can free the surgeon's second hand to assist in the procedure, they often suffer the drawbacks of excess weight, poor balance, mechanical complexity and high expense.

Surgeons performing cataract removal and IOL insertion prefer to execute the procedure expeditiously in order to minimize potential to further traumatize the eye. Additionally, many eye clinics schedule successive procedures closely together in order to utilize the surgeon's time most efficiently. Further, additional handling of lenses by clinic personnel risk damaging the IOLs from handling or misloading them into cartridges and IOL folders which could result in complications during their delivery to the patients eye. Makers of IOLs, recognizing this need for efficiency and error proofing have therefore begun providing IOLs prepackaged sterile, in cartridges having the folder already attached (see, for example, United States Patent Application Publication No. 2007/0270881). Others have designed special IOL receiving cartridges to simplify loading of IOLs for the clinician in order to reduce human error. These cartridges and IOL folders may be provided as an integral part of the overall delivery device (shown, for example, in United States Patent Application Publication Nos. 2013/0226193 and 2014/0200589) or in many instances are provided to be retained by special receiving features built into a universal delivery device containing the necessary plunger and drive mechanism to push a lens through the cartridge and folder and into an eye (shown, for example, in U.S. Pat. No. 7,156,854).

Typically, makers of IOLs have developed dedicated cartridges and folders that work best with their lens design. Further, these lens makers have, in many cases, developed bespoke plunger tip geometries (examples are shown in, for example, U.S. Pat. Nos. 6,733,507; 8,114,095; 8,308,736; 8,758,433; and 8,998,983; as well as United States Patent Application Publication Nos. 2008/0086146; 2010/0217273 and 2010/0228261) for the plunger that works best with the features and design of their specific lens, cartridge and folder members.

SUMMARY

An object of an embodiment of the present invention is to provide an improved IOL delivery device.

Briefly, an embodiment of the present invention provides an IOL delivery device which has a macro movement actuator which is actuateable to move an IOL into position in the device for the IOL to be delivered, and a micro movement actuator which is actuateable to deliver the IOL to the eye.

BRIEF DESCRIPTION OF THE DRAWINGS

The organization and manner of the structure and operation of the invention, together with further objects and advantages thereof, may best be understood by reference to the following description taken in connection with the accompanying drawings wherein like reference numerals identify like elements in which.

DESCRIPTION OF ILLUSTRATED EMBODIMENTS

Figure 1:
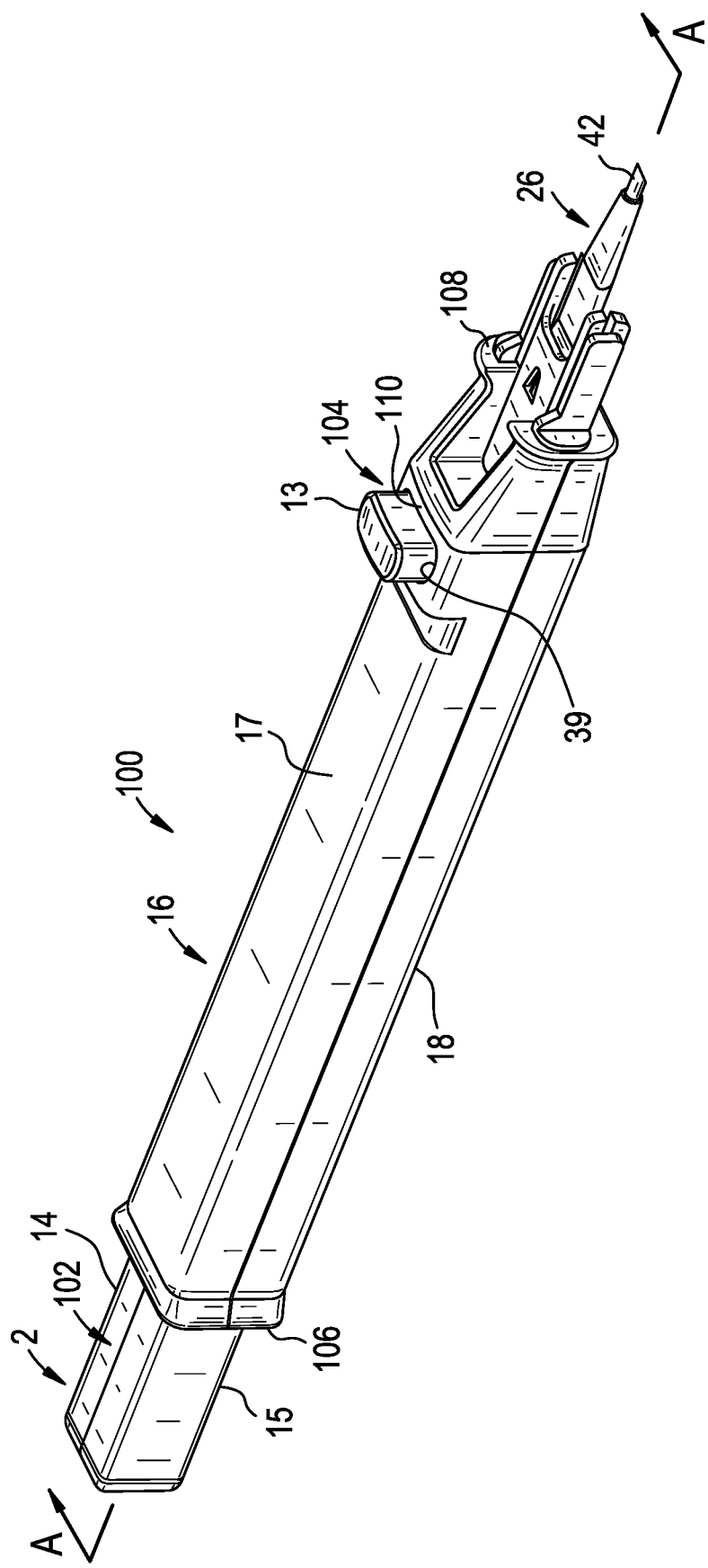
FIG. 1 is a perspective view of an IOL delivery device which is in accordance with an embodiment of the present invention.

While this invention may be susceptible to embodiment in different forms, there are shown in the drawings and will be described herein in detail, specific embodiments with the understanding that the present disclosure is to be considered an exemplification of the principles of the invention, and is not intended to limit the invention to that as illustrated.

FIG. 1 is a perspective view of an IOL delivery device 100 which is in accordance with an embodiment of the present invention. The device 100 is configured to deliver an IOL 24 (see FIGS. 2, 10 and 11 which show the IOL 24) which is disposed in an IOL cartridge 25 which is engaged with, or integral with, the device 100.

The IOL delivery device 100 preferably comprises a macro movement actuator 102 and a micro movement actuator 104. While the macro movement actuator 102 is configured to move the IOL 24 into position within the IOL cartridge 25 for subsequent delivery (as shown in the progression from FIG. 2 to FIG. 10), the micro movement actuator 104 is configured to effect precise delivery of the IOL 24 out the IOL cartridge 25 (as shown in the progression from FIG. 10 to FIG. 11). This will be described in more detail later herein.

Figure 2:
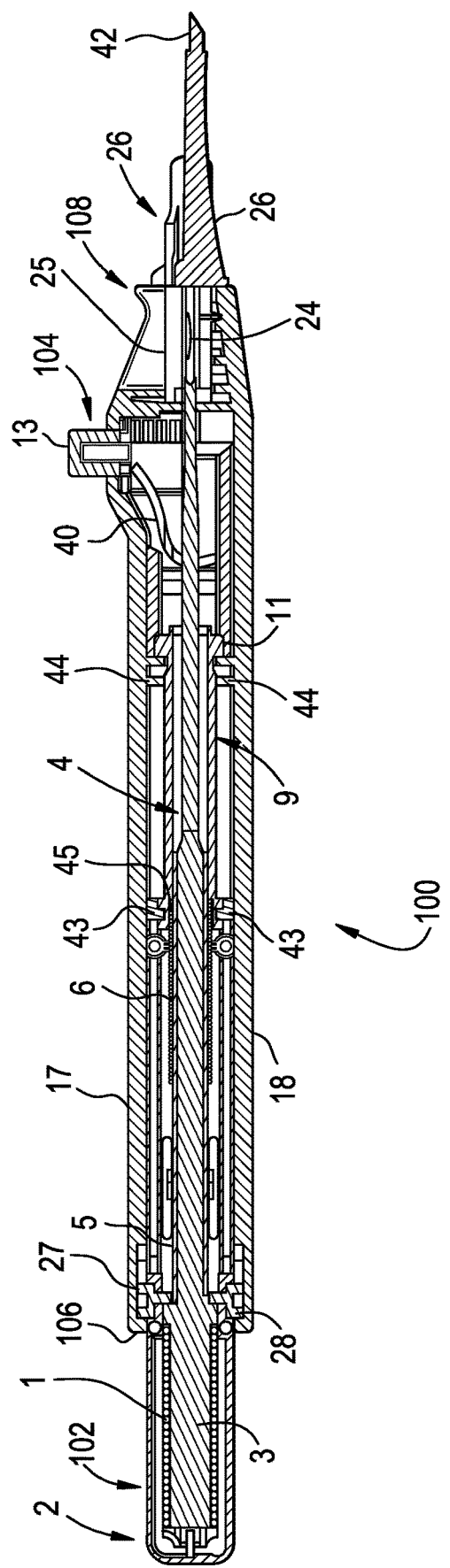
FIG. 2 is a cross-sectional view of the IOL delivery device shown in FIG. 1, taken along line A-A of FIG. 1.
Figure 10:
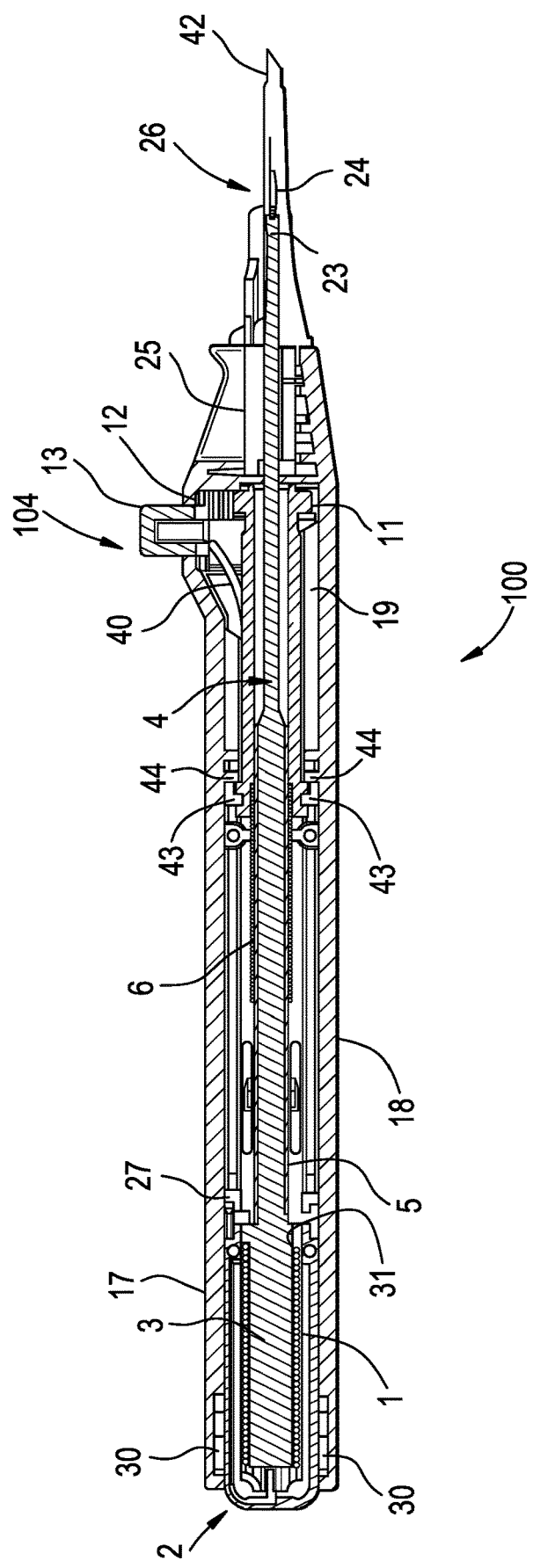
FIG. 10 is a view similar to FIG. 2, but shows the IOL delivery device after the plunger button of the device has been pushed.
Figure 11:
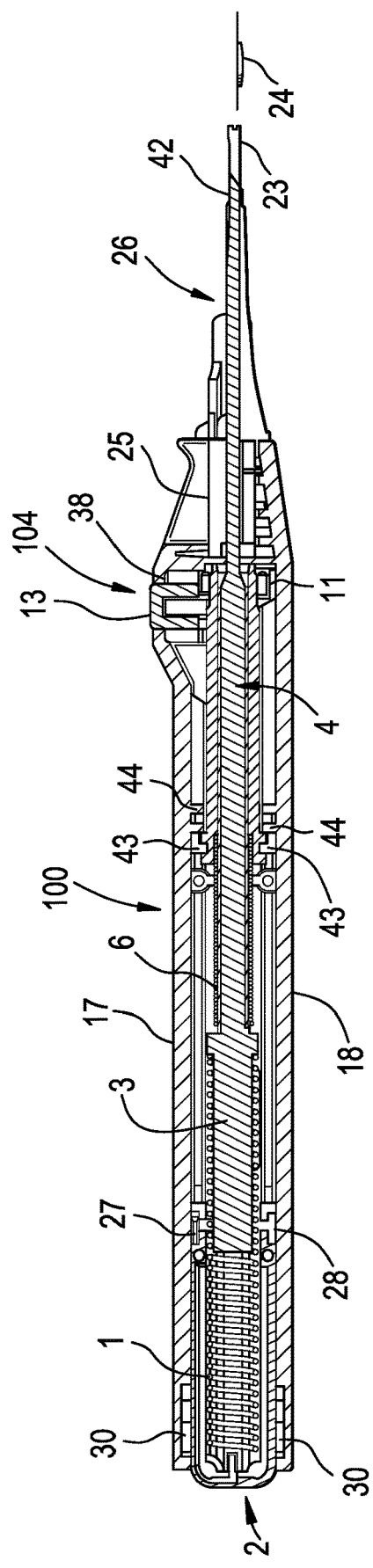
FIG. 11 is a view similar to FIG. 10, but shows the IOL delivery device after the IOL delivery device has delivered the IOL.

As shown in FIG. 1, preferably the IOL delivery device 100 comprises a housing or housing assembly 16. While preferably the macro movement actuator 102 extends from one end 106 of the housing 16, the other end 108 of the housing 16 engages the IOL cartridge 25 which has an IOL 24 retained therein (as shown in FIGS. 2, 10 and 11), and the micro movement actuator 104 is disposed on the side or top 110 of the housing 16. However, the macro and micro movement actuators can be provided on other locations on the housing 16 other than at the end 106 and on the top 110.

Preferably, the housing 16 comprises a housing assembly wherein a housing top 17 and a housing bottom 18 join together to form the housing 16. As such, the terms "housing" and "housing assembly" are used interchangeably herein.

The macro movement actuator 102 may comprise a plunger button 2 which comprises two halves 14, 15 which join together to form the plunger button 2, and the plunger button 2 extends out the end 106 of the housing 16. The opposite end 108 of the housing 16 engages an IOL cartridge 25 which has an IOL 24 disposed therein, and which comprises an IOL folder 26 which has a tip 42. When the IOL delivery device 100 is used to deliver the IOL 24 disposed therein, the IOL 24 gets delivered out the tip 42 of the IOL folder 26, as shown in FIG. 11. The operation of the IOL delivery device 100 will be described in more detail later herein, but first the structure of the IOL delivery device 100 will be described in more detail.

As shown in FIG. 2, inside the device 100 is disposed a plunger 4. The plunger 4 includes an extension 3 which extends into and centers the plunger button 2, and also preferably includes a flange 46 (see FIG. 4) which provides a spring perch 31. A drive spring 1 is disposed inside the plunger button 2, and (as shown in FIG. 2) extends between an inside surface of the plunger button 2 and the spring perch 31 provided by the flange 46 on the plunger 4. While an extension 3 is provided at one end of the plunger 4, preferably the other end of the plunger 4 provides the tip 23 (see FIG. 4) for delivering the IOL 24 out of the IOL folder 26.

Figure 3:
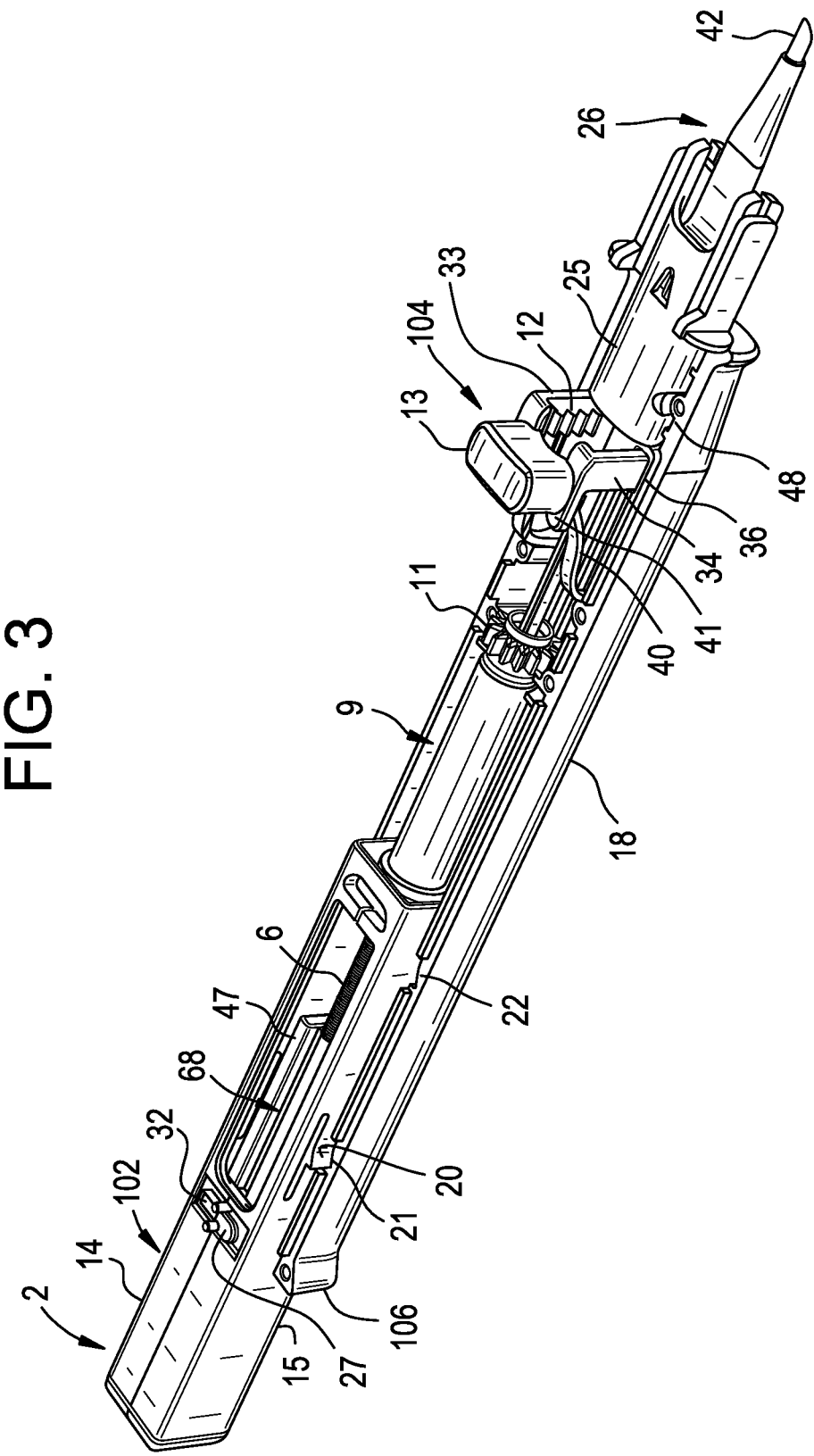
FIG. 3 is a view similar to FIG. 1, but omits some components of the IOL delivery device, so internal components can be more readily seen.
Figure 4:
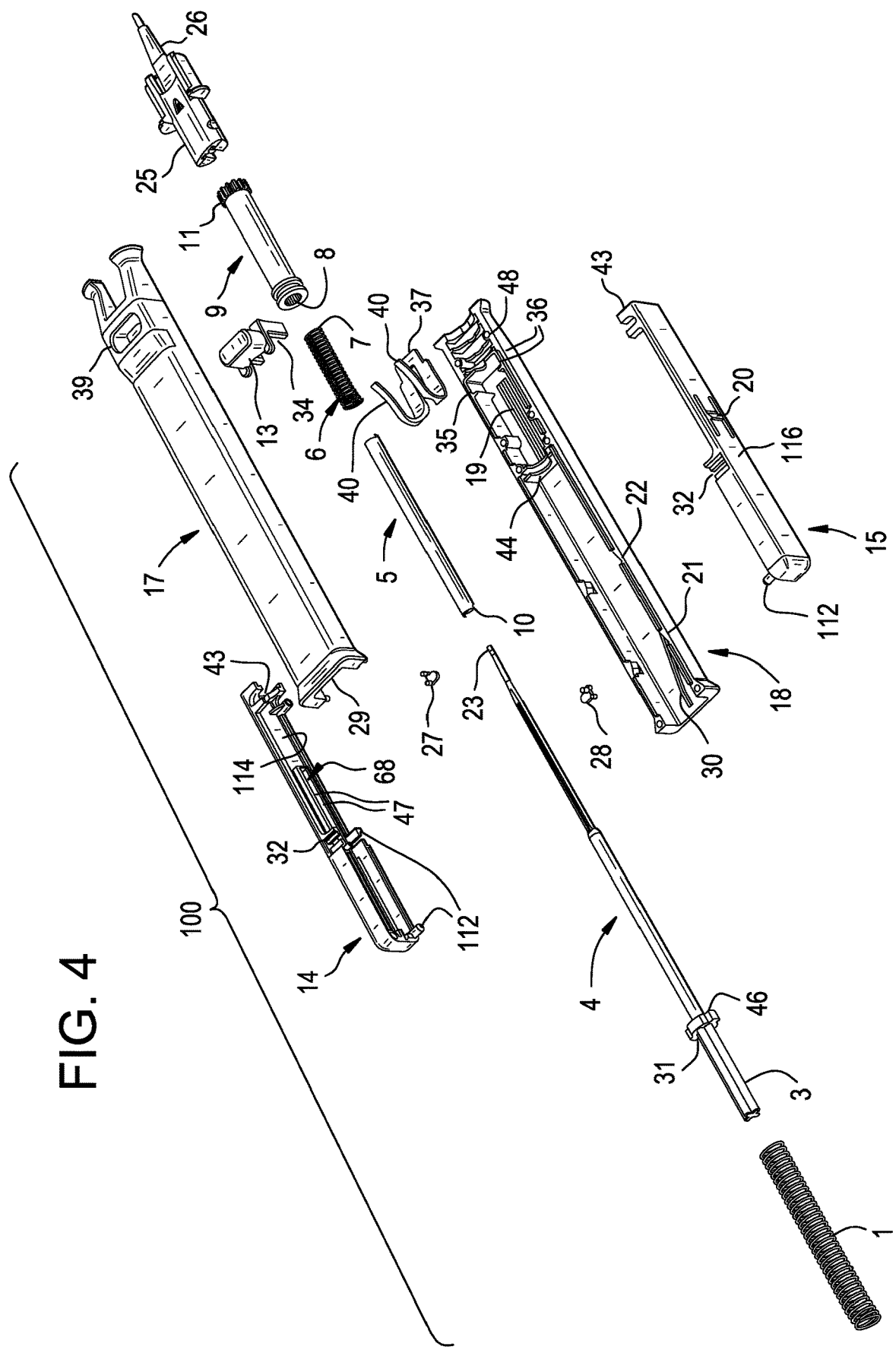
FIG. 4 is an exploded view of the IOL delivery device shown in FIG. 1.
Figure 5:
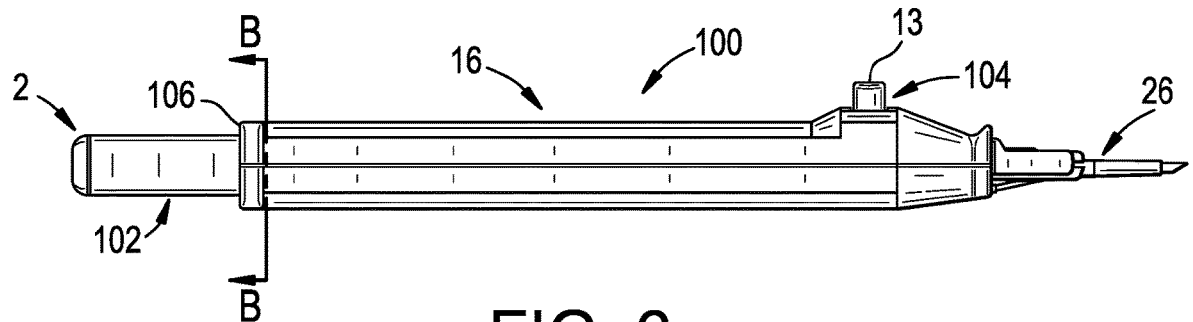
FIG. 5 is a side view of the of the IOL delivery device shown in FIG. 1, showing the IOL delivery device before a plunger button of the device is pushed.
Figure 6:
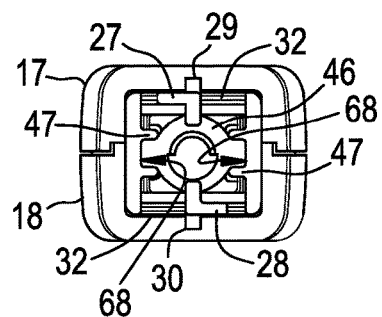
FIG. 6 is a cross-sectional view of the IOL delivery device shown in FIG. 5, taken along line B-B of FIG. 5.

As shown in FIG. 4, preferably each plunger button half 14, 15 includes mating structure 112 for facilitating the joining of the two halves 14, 15 together to form the plunger button 2. This structure 112 may work in a snap fit arrangement or may be bonded together, for example. Preferably, each of the plunger halves 14, 15 includes a guide rail 47 on its inside surface 114 for engaging, such as by orienting and guiding, the flange 46 on the plunger 4, and keeping the plunger 4 from rotating inside the device 100. Additionally, each of the plunger halves 14, 15 preferably includes a deflectable latch 20 on its external surface 116 which engages in one of two receiving notches 21, 22 provided on the housing 16 (see FIG. 3, for example). Preferably, one pair of receiving notches 21 on the housing 16 defines a first position of the plunger button 2, and another pair of receiving notches 22 on the housing 16 defines a second position of the plunger button 2. Specifically, preferably the deflectable latches 20 on the plunger button 2 are disposed in the first pair of notches 21 on the housing 16 before the plunger button 2 is pushed into the housing 16. Then, when the plunger button 2 is pushed into the housing 16, preferably the deflectable notches 20 deflect inward, and the plunger button 2 advances into the housing 16 until the deflectable notches 20 reach and reflect into the second pair of notches 22 on the housing 16, thereby limiting any further movement of the plunger button 2 within the housing 16.

Preferably, each half 14, 15 of the plunger button 2 comprises a portion of a traverse slot 32 such that when the two plunger button halves 14, 15 are joined, they together form the traverse slot 32. The function of the traverse slot 32 will be described in more detail later herein.

Also disposed in the plunger button 2 is a revolving spring clutch 6 which selectively constrains and releases a wear sheath 5 which is disposed radially inward of the revolving spring clutch 6. The wear sheath 5 is proximate the plunger 4, and preferably includes a notch 10 at an end thereof which tends to prevent the wear sheath 5 from rotating relative to the plunger 4 during use. During use, when the revolving spring clutch 6 tightens and constrains around the wear sheath 5, the wear sheath 5 contacts the plunger 4 and prevents the plunger 4 from moving along the longitudinal axis of the IOL delivery device 100. This will be described in more detail later herein. The wear sheath 5 is provided to allow a broader choice of materials for the manufacture of the plunger 4; however, the wear sheath 5 could very well be omitted, depending on the properties of the material chosen for the plunger 4.

Preferably, a rotating sleeve 9 is disposed inside the housing 16, forward of the plunger button 2, jornalled in a bearing provided in the housing 16, wherein the bearing is provided via bearing sections 43 provided on the plunger button halves 14, 15 and bearing sections 44 provided on the housing halves 17, 18. Preferably, the rotating sleeve 9 includes a spring engagement pocket 8 for receiving a portion of the revolving spring clutch 6, and includes a thrust shoulder 45 therein (see FIG. 2) for engaging a spring pawl 7 at the end of the revolving spring clutch 6. Preferably, the rotating sleeve 9 also has a pinion 11 on its external surface for engagement by the micro movement actuator 104.

The revolving spring clutch 6 is preferably sized to grip tightly upon the outermost cylindrical wear surface of the plunger 4, via the wear sheath 5 (if provided). Spring pawl 7 on the distal end of the revolving spring clutch 6 is engaged within the spring engagement pocket 8 of the rotating sleeve 9, and provides for the one-way rotation of the revolving spring clutch 6 whenever rotating sleeve 9 is turned in a direction counter to the wire wind direction of the revolving spring clutch 6. The revolving spring clutch 6 bears against the thrust shoulder 45 on the interior of the spring engagement pocket 8, to transfer longitudinal force provided by the drive spring 1 to the rotating sleeve 9. In order to provide for its rotation, the rotating sleeve 9 is journaled into bearing 43 formed at the distal end of plunger button 2 and bearings halves 44 formed in housing bottom 18 and housing top 17. The inner diameter of the spring engagement pocket 8 and its depth are preferably sized to centralize the revolving spring clutch 6, limit its expansion and engage the revolving spring clutch 6 sufficiently to control it during operation. The drive spring 1 in the plunger button 2 is maintained in a compressed state within the plunger button 2 by the revolving spring clutch 6 that bears against the thrust shoulder 45 of the rotating sleeve 9.

Figure 9:
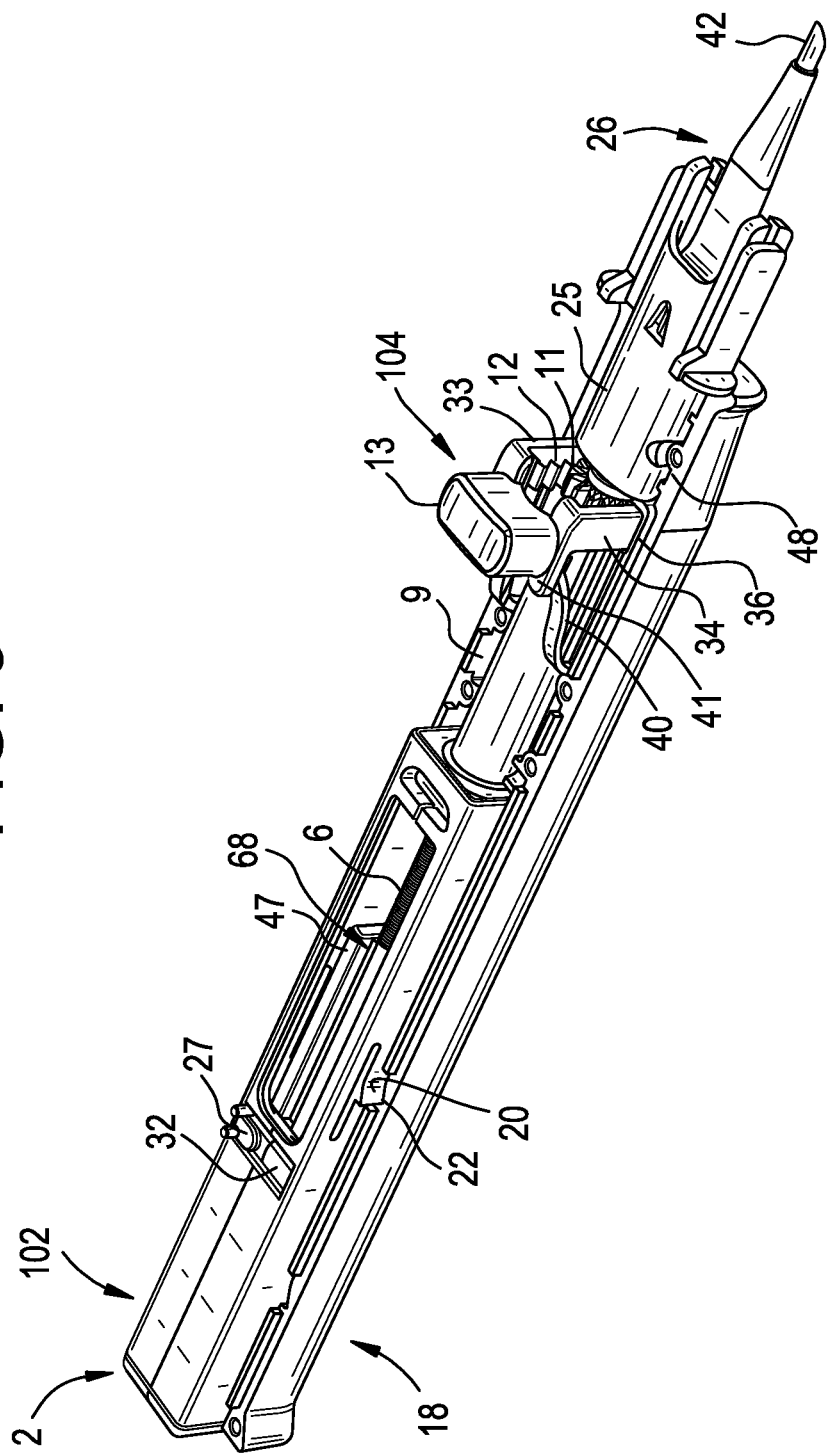
FIG. 9 is a view similar to FIG. 3, but shows the IOL delivery device after the plunger button of the device has been pushed.

The micro movement actuator 104 preferably comprises a control button 13 which extends out a button aperture 39 (see FIG. 1) which is provided in the top half 17 of the housing 16. Preferably, as shown in FIGS. 3 and 9, a pair of legs 33, 34 extend down from the control button 13, and one of the legs 33 has a gear rack 12 thereon which mates with the pinion 11 on the rotating sleeve 9 (see FIG. 9). Each of the housing halves 17, 18 has a pair of pockets 35, 36 (see FIG. 4) configured to receive the legs 33, 34 of the micro movement actuator 104 (see FIGS. 3 and 9).

Preferably, a return spring means such as return spring 37 is disposed in the housing 16, and the return spring 37 is configured to support and spring bias the control button 13 to its original, non-pressed position (shown in FIG. 10). Specifically, as shown in FIG. 4, preferably the control spring 37 includes fingers 40 which bear on the underside of the flanges 41 (see FIGS. 3 and 9) to urge the control button 13 upwards and return it to its original position whenever control button 13 has been pressed downward. The flanges 41 formed at the top of the control button 13 by legs 33 and 34 are provided to abut a button stop 38 (see FIG. 11) which is preferably located under the edge of the button aperture 39 provided in the housing top 17. The return spring means can take many forms. For example, instead of being provided as a leaf spring as shown in the Figures, the return spring means can be provided as being small coil springs under each leg 33, 34 of the button 13. It would depend on the space available within the device.

Figure 7:
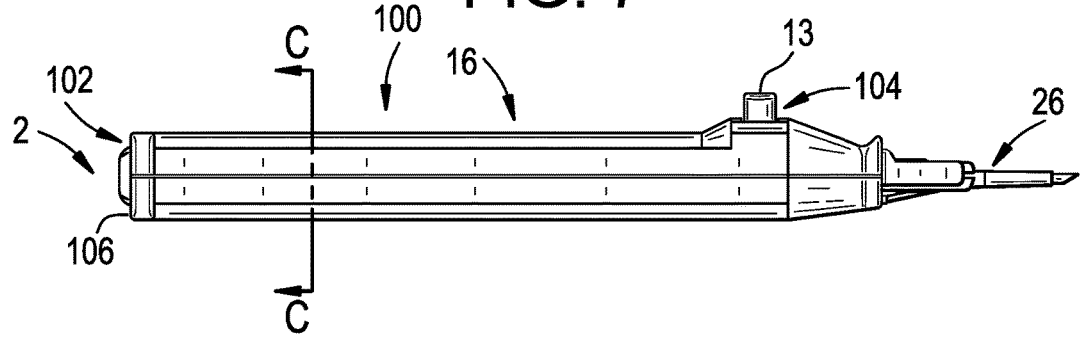
FIG. 7 is a side view of the of the IOL delivery device shown in FIG. 1, showing the IOL delivery device after the plunger button of the device has been pushed.

As shown in FIG. 4, preferably the housing bottom 18 includes a synchronizing rail 19 which functions to facilitate engagement of the pinion 11 on the rotating sleeve 9 with the gear rack 12 on the micro movement actuator 104 (as shown in FIG. 9). The synchronizing rail 19 is configured to prevent rotation of the pinion 11 until the plunger button 2 has been advanced to its second position within the housing 16, and assures that the pinion 11 is correctly oriented to smoothly engage the teeth of gear rack 12 when the plunger button 2 is advanced from its first position shown in FIGS. 1, 2, 3 and 5, to its second position shown in FIGS. 7, 9 and 10. Preferably, the synchronizing rail 19 terminates just short of the pinion's operating area, such that the pinion 11 is only free to rotate after the plunger button 2 has been advanced fully to its second position (as shown in FIGS. 7, 9 and 10), and the latches 20 of the plunger button 2 have engaged the second set of receiving notches 22 of the housing 16.

Preferably, a pair of safety stops 27, 28 are provided (see FIGS. 4, 6 and 8), wherein a top safety stop 27 rides along a guide track 29 provided in the top half 17 of the housing 16, and a bottom safety stop 28 rides along a guide track 30 provided in the bottom half 18 of the housing 16. Preferably, each of the safety stops 27, 28 resides within a corresponding traverse slot 32 (see FIGS. 3 and 9) provided on the top and bottom of the plunger button 2, serving as sears to prevent unintended advancement of the plunger 4 during handling, transportation and storage.

In the present embodiment, an IOL 24 retained within the IOL deliver device 100 can be moved from its retained position, to a pre-staged position within an IOL folder 26 (as shown in FIG. 2), to a staged position immediately preparatory to delivery within an eye (as shown in FIG. 10), to final delivery from the folder tip (as shown in FIG. 11) into an eye.

Turning the rotating sleeve 9 in the direction opposite the wind of the revolving spring clutch 6 causes the spring pawl 7 of the revolving spring clutch 6 to engage the spring engagement pocket 8 of the rotating sleeve 9. Further turning of the rotating sleeve 9 in this direction causes a radial expansion of the revolving spring clutch 6, which releases some of its grip upon the wear sheath 5 and, in turn, allows the plunger 4 to traverse distally along its longitudinal axis in response to the force exerted by the compressed drive spring 1 against the spring perch 31 on the plunger 4. The longitudinal movement of the plunger 4 will continue as long as the rotating sleeve 9 is turned in the direction opposite the wind of the revolving spring clutch 6, and will discontinue when the revolving spring clutch 6 recovers its compressive grip upon the wear sheath 5, or until the flange 46 of the plunger 4 reaches its allowed travel limit within at least one guideway 68 which is provided inside the plunger button 2. As the plunger 4 is released by the spring clutch 6 to traverse along its longitudinal axis, the drive spring 1 begins to expand from its compressed condition within the plunger button 2. In some of the Figures, each guideway 68 is shown as being specifically provided by two spaced-apart guide rails 47, but still other structures and arrangements are entirely possible while still staying within the scope of the present invention.

Conversely, whenever the rotating sleeve 9 is turned in the same direction as the wire wind of the revolving spring clutch 6, the spring pawl 7 of the revolving spring clutch 6 releases its engagement from the spring engagement pocket 8 of the rotating sleeve 9, which in turn allows the rotating sleeve 9 to turn free from the positive rotational driving engagement provided by the spring pawl 7. This release of the spring pawl 7 from the spring engagement pocket 8 of the rotating sleeve 9 allows the revolving spring clutch 6 to maintain a secure grip upon the wear sheath 5 (or directly on the plunger 4, if the wear sheath 5 is not provided) in order to prevent any longitudinal movement of the plunger 4 when, for example, the rotating sleeve 9 is returned to its original position.

As previously discussed, the end of the rotating sleeve 9 (opposite from the spring engagement pocket 8) is provided with pinion 11 to engage the gear rack 12 of the control button 13. This pinion 11 can be brought into contact with the gear rack 12 when the plunger button 2 is advanced longitudinally from its first position within the housing assembly 16 as shown in FIGS. 2 and 3, to its second position within the housing assembly 16 as shown in FIGS. 9 and 10.

The first position of the plunger button 2 is maintained by the engagement of the deflectable plunger button latches 20 with the first pair of receiving notches 21 as shown in FIG. 3. The second position of the plunger button 2 occurs through the advancement of the plunger button 2 beyond the first engagement position, whereby the latches 20 disengage from the receiving notches 21 of the housing assembly 16, to the second engagement position in which the latches 20 engage the second pair of receiving notches 22 of the housing assembly 16, i.e., at the limit of travel for the plunger button 2, as shown in FIG. 9. When the plunger button 2 is moved in this manner, the rotating sleeve 9 traverses longitudinally within the bearing halves 44, and the plunger tip 23 advances from its initial position behind the IOL 24 into a lens staging position at the entry portion of the IOL folder 26, as shown in FIG. 10, and the pinion 11 of the rotating sleeve 9 engages the gear rack 12 of the control button 13.

With advancement of the plunger button 2 from its first position (see FIGS. 1-3 and 5) to its second position (see FIGS. 7, 9 and 10), the IOL 24 is urged along by the plunger tip 23 from its preloaded position in the IOL cartridge 25 to a pre-staged position at the entry of the IOL folder 26.

While the plunger button 2 is located in its first engagement position (see FIGS. 1-3 and 5), the spring 1 is retained in its compressed position within the plunger button 2 by the grip of the revolving spring clutch 6 upon the wear sheath 5 as well by safety stop 27 which engages the guide track 29 provided on the inside surface of the housing top 17, and safety stop 20 which engages the guide track 30 provided on the inside surface of the housing bottom 18. At the first engagement position of plunger button 2, safety stops 27 and 28 rest in front of spring perch 31 of the extension 3 on the plunger 4.

Figure 8:
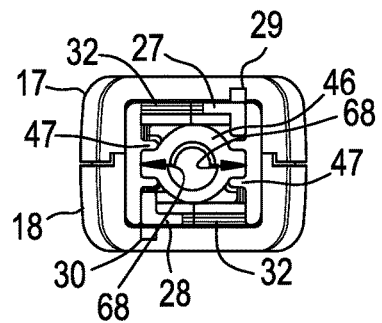
FIG. 8 is a cross-sectional view of the IOL delivery device shown in FIG. 7, taken along line C-C of FIG. 7.

Advancement of the plunger button 2 from its first position to its second position (see FIGS. 7, 9 and 10) within the housing assembly 16 causes the top safety stop 27 and the bottom safety stop 28 to traverse from their stop position (see FIG. 6) within the top guide track 29 and bottom guide track 30, respectively, and move away from their central safety position in slots 32 into a ready position at the edge of slots 32 (see FIG. 8). When in the ready position, safety stops 27 and 28 no longer obstruct the longitudinal passage of flange 46 of the plunger 4, and therefore are clear from inhibiting longitudinal movement of the plunger 4 within the plunger button 2.

Actuating the micro movement actuator 104, i.e., by pressing control button 13 down as shown in FIG. 11, moves the gear rack 12 downward, causing the engaged pinion 11 to rotate in response. This rotation of the pinion 11 and the integral rotating sleeve 9, of which the pinion 11 is part, causes the spring engagement pocket 8 to catch against the spring pawl 7 of the revolving spring clutch 6, and subsequently begin to rotate the revolving spring clutch 6 in the same direction, against the spring's direction of wind, thereby releasing the radial tension of the revolving spring clutch 6 upon wear sheath 5, and allowing the plunger 4 to advance longitudinally in reaction to the force of the compressed drive spring 1.

When the control button 13 is released, the fingers 40 of the return spring 37 bear on the underside of the flanges 41 to urge control button 13 upwards and return it to its original position. When the control button 13 is released and allowed to be returned to its original position by the restorative force of the return spring 37, the pinion 11 along with its integral rotating sleeve 9 is caused to rotate in the opposite direction, whereupon the interior of the spring engagement pocket 8 turns free of engagement with the spring pawl 7 to allow the revolving spring clutch 6 to retain its radial tension on the wear sheath 5. In this manner, pressing down on the control button 13 allows the plunger 4 to move longitudinally in order to advance and deliver the IOL 24 distally through the IOL folder 26 into an eye.

The rate by which the IOL 24 is advanced through the folder 26 is dependent upon the distance the control button 13 is pressed, the number of times the control button 13 is pressed, and the rate of frequency at which control button 13 is pressed. From a design aspect, the rate at which the IOL 24 is delivered can further be impacted by the length of the revolving spring clutch 6, its number of coils engaged upon the outermost cylindrical surface of the plunger 4 as provided, in this specific embodiment, by wear sheath 5. Further, the ability of the revolving spring clutch 6 to restrain and control the force of the compressed drive spring 1 is dependent upon the number of coils within control spring 6, the radial tension each coil exerts upon the outermost cylindrical surface of the plunger 4, and the coefficient of friction between the control spring 6 and the outermost cylindrical surface of the plunger 4.

It should be noted that although the example herein utilizes the engagement of a rack equipped control button 13 and a pinion 11 mounted to a rotating sleeve 9, the rotating sleeve 9 could also be actuated by other means, such as by means of a lever mounted to the rotating sleeve 9 in place of the pinion 11. Such a lever could be pivoted from side to side in order to sequentially engage and release the rotating sleeve 9 in order to achieve the same type of reciprocating motion one obtains by pressing and releasing the control button 13.

In practice, the IOL delivery device 10 could be supplied to a user with drive spring 1 compressed within plunger button 2, with plunger button 2 residing in its first position as best shown in FIG. 3, and with the plunger tip 23 in its initial position not yet in contact with the IOL 24. At this point, the IOL delivery device may be supplied to a user, for example: 1) with an integral IOL retention feature 48 (see FIG. 4) in place ready to accept the IOL 24 and IOL folder 26; 2) with a factory preloaded IOL cartridge 25 and IOL folder 26 in place; 3) with an IOL cartridge 25 in place ready to receive an IOL 24 and IOL folder 26; 4) ready to accept a previously loaded IOL cartridge 25 with IOL folder 26; or 5) ready to accept an IOL folder 26 that the user has loaded with an IOL 24.

With the IOL cartridge 25 and/or IOL folder 26 in place on the delivery device 100 and an IOL 24 in place within, lens deployment would be obtained by the user first filling the IOL folder 26 with approximately 0.2 ml of Ophthalmic Viscosurgical Device ("OVD"), such as B&L Amvisc, AMO Healon or Alcon Viscoat, in order to lubricate passage of the IOL 24 through the IOL folder 26.

Next, the user pushes the plunger button 2 into the device housing assembly 16 until the plunger button 2 latches into its second position as best shown in FIG. 9, whereby safety stops 27 and 28 have moved fully out of the path of the plunger 4 (see FIG. 8). Placing plunger button 2 in its second position also causes the plunger tip 23 to advance longitudinally and contact the IOL 24 to pre-stage it within the IOL folder's entrance funnel. At the surgeon's request, the surgical assistant may advance the IOL 24 within the IOL folder 26 by depressing the control button 13, perhaps more than once, in order to move the IOL 24 deeper into the IOL folder 26, to stage it at a location near the folder tip 42. The IOL 24 will then be staged ready for deployment, and preferably is not allowed to remain in this condition for more than sixty seconds. The surgical assistant immediately hands the ready staged IOL delivery device 100 to the surgeon who inserts the IOL folder tip 42 into a small, previously prepared incision at the cornea of an eye, places the folder tip 42 in alignment with the previously prepared capsular sac and then depresses the control button 13 as necessary in order to allow the plunger 4 to advance fully within IOL folder tip 42 as shown in FIG. 11, and deliver the IOL 24 from the IOL folder 26 into an eye.

It should be noted that an example of a retention means 48 for interfacing with and retaining a preloaded IOL cartridge 25 with IOL folder 26 or a manually loaded IOL folder 26 is illustrated herein strictly to provide a model to demonstrate how this task could be accomplished. The IOL delivery device so disclosed can be equipped with the necessary features for the proper engagement of any number of IOL manufacturer's proprietary cartridges and folder mechanisms, as previously stated, through provision of the required retaining section for any specific cartridge and/or folder. Such retaining modifications, examples of which are shown in, for example, U.S. Pat. Nos. 8,114,095; 8,758,433 and 8,998,983, as well as United States Patent Application Publication No. 2008/0086146, do not materially detract from or alter the operation of this IOL delivery device, its internal mechanisms or, the basis upon which the device is intended to function or, the device's method of use.

The IOL delivery device disclosed herein has been conceived to be able to be equipped with the necessary customized features required to mate with any IOL maker's proprietary cartridge and folder assembly, provided that the cartridge and folder system relies upon a plunger rod to drive the lens through the folder for delivery. Further, the plunger on the embodiment described herein can be detailed with the preferred proprietary tip geometry specified by the IOL maker in order to work with the IOL maker's folder and insertion product.

An embodiment of the present invention is therefore conceived to be an inexpensive self-powered, single hand use, potentially disposable, light weight and convenient IOL delivery mechanism that is easily operable and provides a plunger with the required motive power to stage, advance and efficiently deliver an IOL into an eye using conventional proprietary IOL folders. Further, the device is specifically configured to be simple to operate with steps that are familiar and intuitive to users trained upon the manual IOL devices regularly used in eye clinics today. User training for the device disclosed herein should therefore prove easy and intuitive without negative transfer resulting from users previously trained upon traditional manual screw or plunger actuated devices. Additionally, the IOL delivery device disclosed herein is not burdened with the weight typical of electrically driven devices or the drag associated with tethering control wires common to these devices. Therefore, surgeons using the delivery device disclosed herein can better sense and respond to the tactile signals experienced during the IOL implantation procedure.

Figure 12:
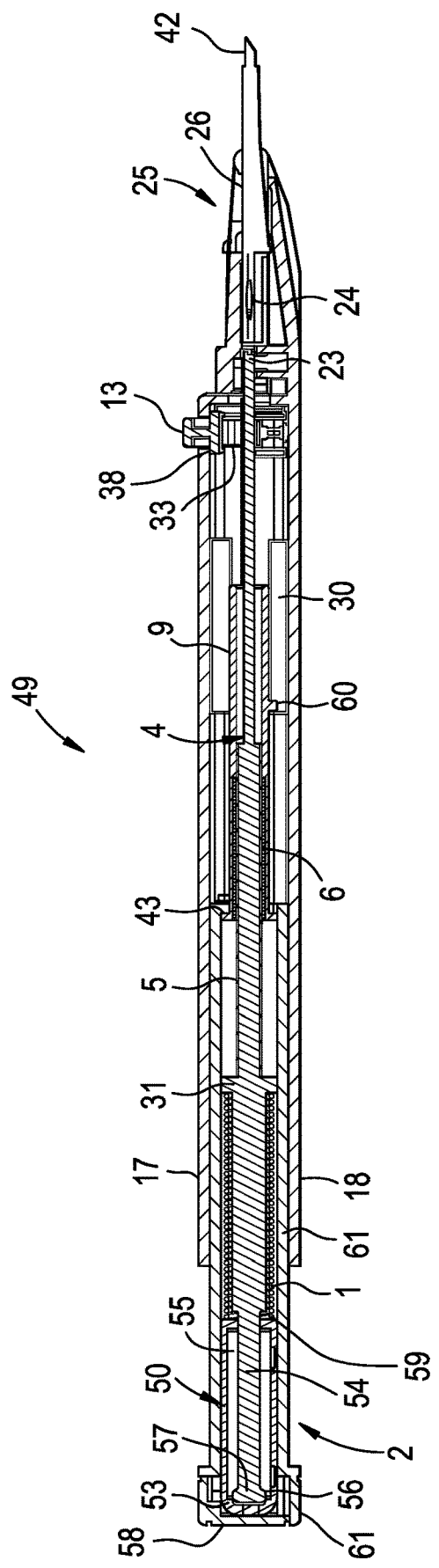
FIG. 12 is a cross-sectional view like FIG. 2, but of an IOL delivery device which is accordance with a second embodiment of the present invention.
Figure 13:
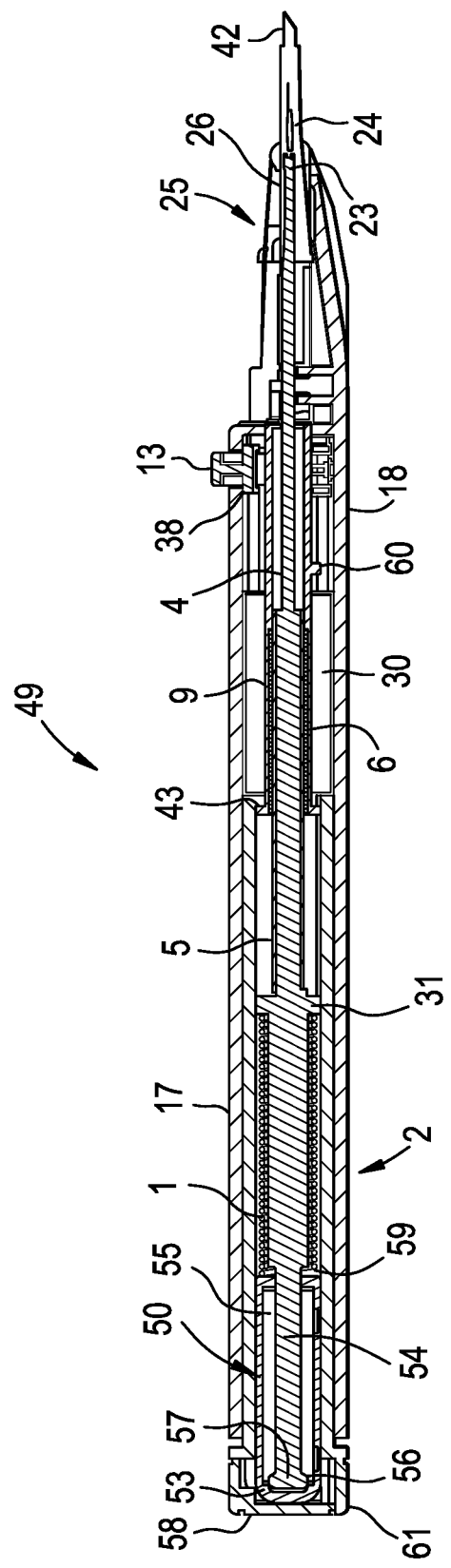
FIG. 13 is a view similar to FIG. 12, but shows the IOL delivery device after the plunger button of the device has been pushed.
Figure 14:
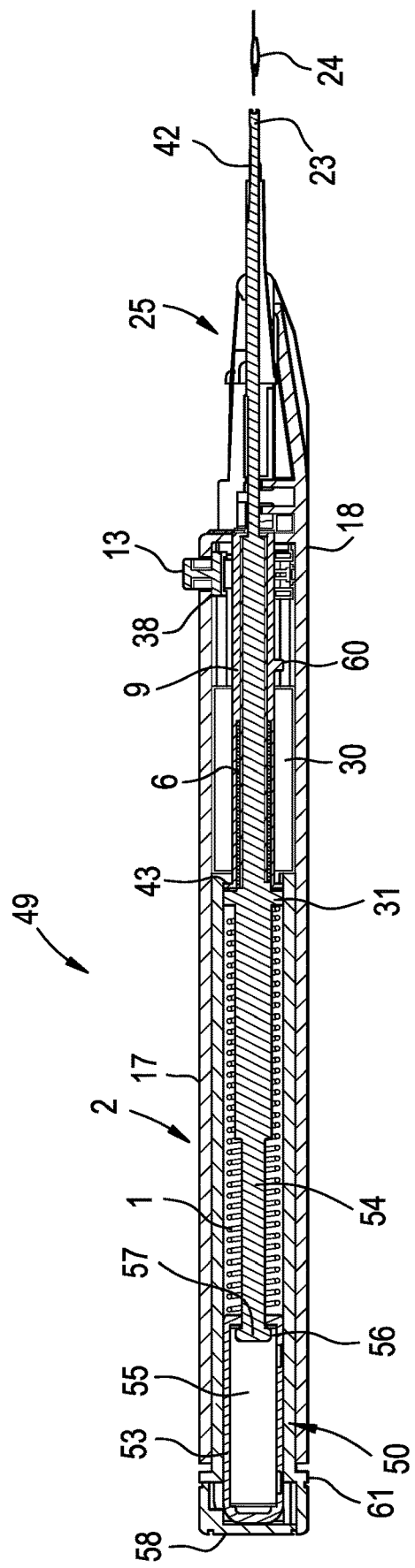
FIG. 14 is a view similar to FIG. 13, but shows the IOL delivery device after the IOL delivery device has delivered the IOL.
Figure 15:
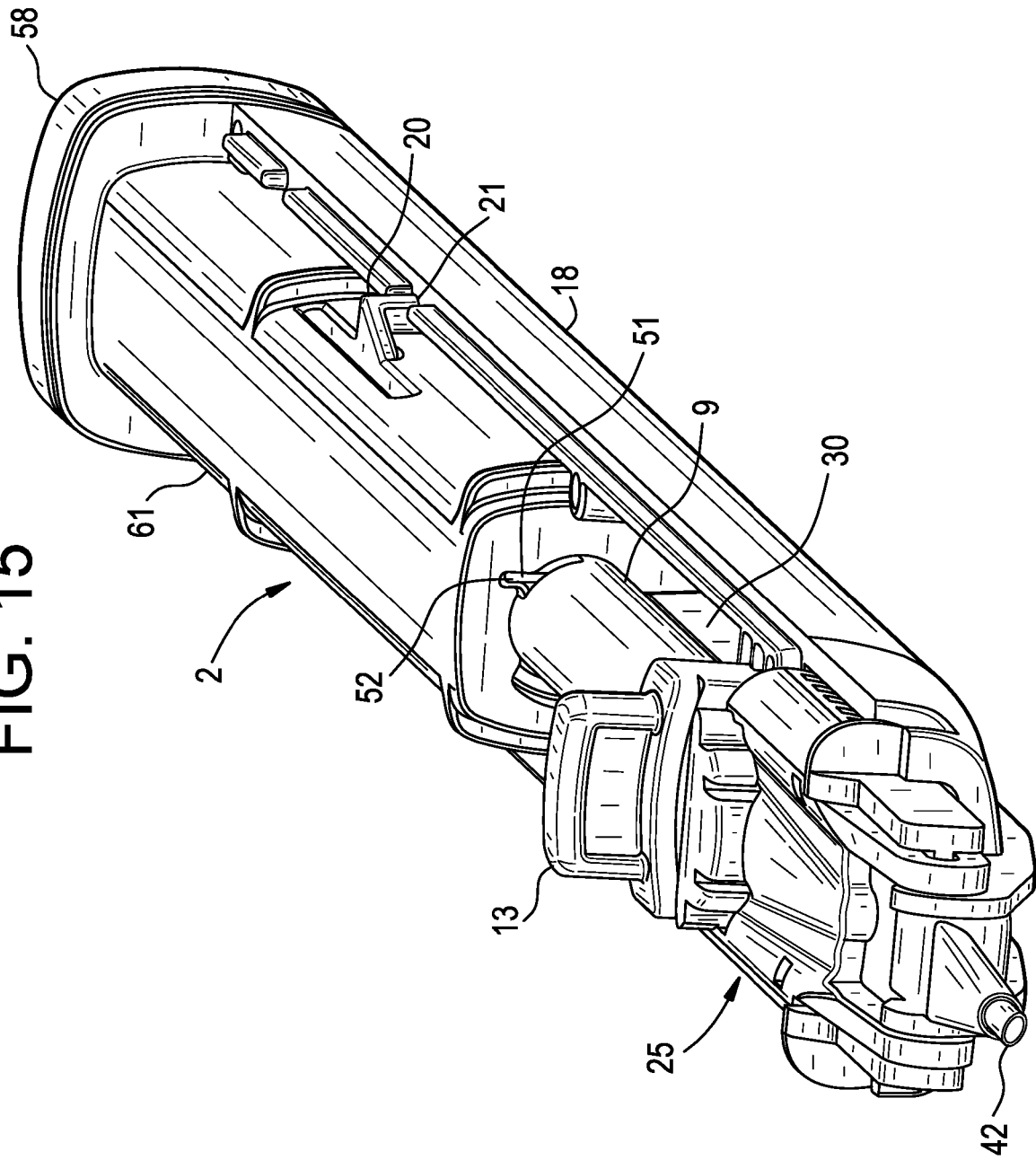
FIG. 15 in an interval view of the IOL device shown in FIGS. 1-14, omitting a housing top (so internal components can be more readily seen), and shows the IOL delivery device after the plunger button of the device has been pushed.

FIGS. 12-15 relate to an improved IOL delivery device 49 which is in accordance with an alternative embodiment of the present invention. The IOL delivery device 49 is very similar to the IOL delivery device 100 in terms of structure and operation, so only the differences will be explained in detail, and like reference numerals are used to identify like parts. Specifically, FIG. 12 is a longitudinally sectioned side view of the improved IOL delivery device 49, shown in its delivered condition prior to use. FIG. 13 is a longitudinally sectioned side view of the improved IOL delivery device 49, shown with the plunger button 2 pressed in, placing the IOL 24 in a staged condition prior to IOL 24 deployment. FIG. 14 is a longitudinally sectioned side view of the improved IOL delivery device 49, shown with the plunger 4 fully extended following IOL 24 deployment. FIG. 15 is an internal view of the improved IOL delivery device 49, without its housing top 17, and with the plunger button 2 placed in the IOL 24 staged position.

The IOL delivery device 49 differs from the IOL delivery device 100 in that the IOL delivery device 49 provides for a more controlled delivery speed of the IOL 24 through the IOL folder 26 and into a patient's eye. The IOL delivery device 100 disclosed previously herein, requires that a user press down on the control button 13, to turn the rotating sleeve 9, which causes the revolving spring clutch 6 to release its grip on the wear sheath 5, to allow the plunger 4 to advance under the force of the drive spring 1 and push the IOL 24 through and out of the IOL folder 26, and into a patient's eye. With the IOL delivery device 100, the advancement of the plunger 4 by a very strong drive spring 1 is thereby controlled by the distance and rate of movement applied by a user to the control button 13. The control button 13 requires relatively little force to operate, although the force of the drive spring 1 that it controls is quite high. With the IOL delivery device 100, depressing the control button 13 a large distance results in more movement of the plunger 4, and pressing control button 13 faster results in faster movement of the plunger 4. However, some users would prefer to simply be able to press down on the control button 13, and allow the device to automatically control the delivery speed of the IOL 24 through IOL folder 26 and into the patient's eye.

The IOL delivery device 49 shown in FIGS. 12-14 provides for this type of operation. With the IOL delivery device 49, the rate at which the user presses the control button 13 down has very little impact upon the speed at which the plunger 4 advances in response to the force of the drive spring 1. The IOL delivery device 49 provides this improvement by (compared to the IOL delivery device 100) adding a linear speed control governor 50 and providing a minor change at the distal free end 51 of the revolving spring clutch 6. This will now be described in detail.

First, the minor change at the distal free end 51 of the revolving spring clutch 6 will be described, and then the structure and function of the linear speed control governor 50 will be described. With regard to the distal free end 51 of the revolving spring clutch 6, in the IOL delivery device 49, the free end 51 of the revolving spring clutch 6 is constrained within a notch 52 (see FIG. 15) provided in the distal end 51 of the improved IOL delivery device's unitary plunger button 61 (see FIGS. 12-14), and therefore prevented from revolving when the control button 13 is depressed by the user to rotate the rotating sleeve 9 by means of the geared connection between the control button 13 and the pinion 11. Constraining the free end 51 of the revolving spring clutch 6 against rotation prevents the revolving spring clutch 6 from dissipating the rotational force induced into it by rotating sleeve 9, as is possible in the IOL delivery device 100 described previously. The consequence of this restrained condition is that the revolving spring clutch 6 is prevented from gripping the wear sheath 5 until the actuating force that revolved the rotating sleeve 9, i.e., the user's downward pressure against the control button 13, has been released to allow the control button 13 to be returned to its normal up position. When constrained in this manner, the revolving spring clutch 6 simply effectively becomes a brake that either prevents or allows longitudinal movement of the plunger 4. As such, the rate at which the user presses the control button 13 down has very little impact upon the speed at which the plunger 4 advances in response to the force of the drive spring 1.

Constraining the end 51 of the revolving spring clutch 6 in the notch 52 makes its response to actuation more immediate and operable over a narrower band of rotation. Not constraining the revolving spring clutch 6 (i.e., in the IOL delivery device 100) makes the revolving clutch 6 less responsive, and therefore in demand of more degrees of rotation of the rotating sleeve 9, in order to obtain the same rate of travel of the plunger 4.

In the improved IOL delivery device 49, the advancement speed of the plunger 4 should ideally fall into a range that allows the IOL 24 sufficient time to elastically fold and conform to the IOL folder 26 without suffering permanent deformation. Attempting to drive an IOL 24 through an IOL folder 26 too rapidly can exceed the IOL's ability to properly deform in order to redistribute its mass within the IOL folder 26. When this happens, the plunger tip 23 can puncture or shear the IOL 24, leaving the IOL 24 unserviceable and/or jammed within the IOL folder 26. Advancement of the plunger 4 must therefore be limited to a speed that does not exceed the ability of IOL 24 to achieve the deformation necessary to negotiate the IOL folder 26. A reasonable target speed for certain large diopter IOL's, for example, is 1 mm/sec-4 mm/sec.

Figure 16:
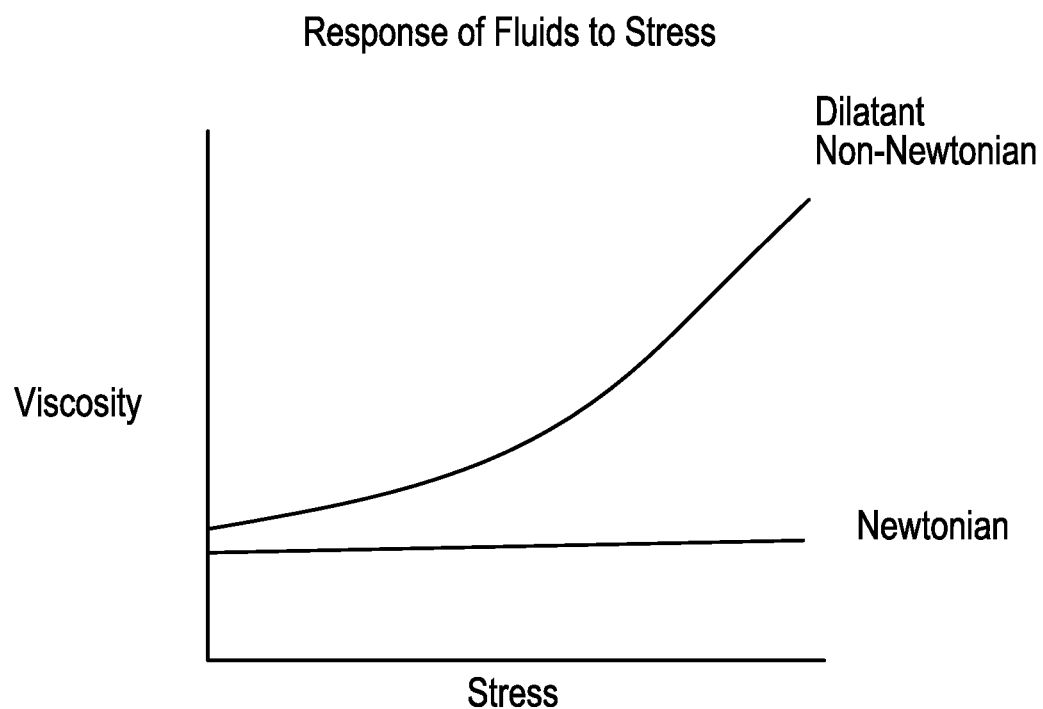
FIG. 16 is a graphic that illustrates the viscosity response of Newtonian fluids and dilatant non-Newtonian fluids when placed under shear stress.

Compared to the IOL delivery device 100, in order to replace the plunger speed control that is lost by effectively converting the revolving spring clutch 6 to an on/off brake, the improved IOL delivery device 49 is preferably equipped with a linear speed control governor 50. Preferably, the linear speed control governor 50 comprises an outer housing 53, a plunger leg 54 having an interference knob 57, and a stable high viscosity dilatant non-Newtonian fluid filling 55. The linear speed control governor 50 is preferably positioned at the proximal end of the drive spring 1, within the plunger button 2. Preferably, the linear speed control governor 50 is retained in place by a plunger button end cap 58, and also serves as a proximal spring perch 59 for the drive spring 1. The dilatant non-Newtonian fluid filling 55, unlike common Newtonian fluids, increases in viscosity when placed under shear stress. A graphic example of the response of a dilatant non-Newtonian fluid subjected to shear stress can best be understood by viewing FIG. 16.

In operation, whenever the plunger control button 13 is pressed down by the user to cause the rotating sleeve 9 to turn the connected spring pawl 7, and thus turn revolving spring clutch 6 when its free end 51 is constrained in notch 52 of a single piece plunger button 2, the revolving spring clutch 6 releases its grip upon the wear sheath 5, thereby allowing the plunger 4 to advance under the urging of the drive spring 1 bearing upon the plunger 4. Releasing the control button 13 and allowing the control button 13 to return to its original uppermost position allows the spring clutch 6 to restore its grip upon the wear sheath 5 and arrest movement of the plunger 4.

Whenever the grip of the spring clutch 6 upon the wear sheath 5 is released by pressing the control button 13 (as described previously), the rate at which the plunger 4 in the improved IOL delivery device 49 advances is controlled by the interaction of the interference knob 57 of the plunger leg 54 and the dilatant non-Newtonian fluid filling 55 contained within the outer housing 53 of the speed control governor 50. More specifically, when a user pushes the control button 13 to allow movement of plunger 4 under the driving force of the drive spring 1, the interference knob 57 on the plunger leg 54 places the dilatant non-Newtonian fluid filling 55 into shear stress. Once placed under shear stress, the viscosity of the dilatant non-Newtonian fluid filling 55 immediately increases as suggested by the example in FIG. 16, and this increased viscosity inhibits the rate at which the interference knob 57 of the plunger leg 54 can progress through the dilatant non-Newtonian fluid 55 and, in turn, slows the rate of advancement of the attached plunger 4 while under the driving force of the drive spring 1. More particularly, placing the dilatant non-Newtonian fluid 55 under shear stress increases its viscosity and causes it to resist rapid bypass flow through the annular space 56 created between the interference knob 57 and the outer housing 53. This reluctance to flow through the annular space 56 slows distal movement of the interference knob 57 and the plunger leg 54 through the dilatant non-Newtonian fluid mass. Therefore, when the plunger 4 is released, i.e., by pressing control button 13, and allowed to advance under the urging of the drive spring 1, its rate of movement is governed by the reluctance of the dilatant non-Newtonian fluid 55 to flow through the annular space 56, due to its elevated viscosity state created by shear stress.

With regard to use, from a user point of view, the method by which the improved IOL delivery device 49 is used does not differ substantially from how the IOL delivery device 100 is used. Filling the IOL cartridge 25 with OVD to lubricate the passage of the IOL 24 remains the same, as does the next step of pressing the plunger button 2 to advance the IOL 24 into a staged condition. In order to assure proper engagement of the teeth of pinion 11 with teeth of the gear rack 12 on the control button 13, the improved rotating sleeve 9 relies upon guide tab 60, which remains engaged with the guide track 30 of the bottom housing 18 until the teeth of the pinion 11 attain partial engagement with the gear rack 12. Actuation of the improved IOL delivery device 49 by pressing the control button 13 still results in movement of the plunger 4 to push the IOL 24 through the IOL cartridge 25. However, with the improved IOL delivery device 49, holding the control button 13 down allows the plunger 4 to continue advancing at a governed rate, dictated by the speed control governor 50.

Assembly of the improved IOL Delivery device 49 is similar to assembly of the IOL delivery device 100 described previously, wherein the housing bottom 18 receives a sub-assembly constructed within the plunger button 2 that is comprised of compressed drive spring 1, plunger 4 with wear sheath 5, spring clutch 6 and rotating sleeve 9 installed within the plunger's button's load bearings structure. The differences in assembling the improved IOL delivery device 49 start with the design of the improved device's unitary plunger button 61, which is preferably a one piece molded part made to receive the above cited components and the speed control governor 50 from its proximal end, all of which are retained in place with the plunger button end cap 58, which is preferably made to snap permanently in place. This approach provides for a more robust plunger button assembly capable of retaining a substantially stronger pre-loaded drive spring 1 compared to the two plunger button halves 14 and 15 of the IOL delivery device 100 described previously. This improved device plunger 2 sub-assembly is placed into the housing bottom 18, followed by the control button 13 with a return spring means, such as, for example, return spring 37, before installation of the housing top 17.

Both devices 100 and 49 provide an IOL delivery device which has a macro movement actuator which is actuateable to move an IOL into position in the device for the IOL to be delivered, and a micro movement actuator which is actuateable to deliver the IOL to the eye. However, device 49 provides an improvement, and is specifically configured to provide that a user simply be able to press down on the control button 13, and allow the device to automatically control the delivery speed of the IOL 24 through IOL folder 26 and into the patient's eye. With the IOL delivery device 49, the rate at which the user presses the control button 13 down has very little impact upon the speed at which the plunger 4 advances in response to the force of the drive spring 1.

FIGS. 17-20 relate to yet a further improved IOL delivery device 149 which is in accordance with a third embodiment of the present invention. The IOL delivery device 149 is very similar to the IOL delivery devices 100 and 49 described previously in terms of structure and operation, so only the differences will be explained in detail, and like reference numerals are used to identify like parts.

Figure 17:
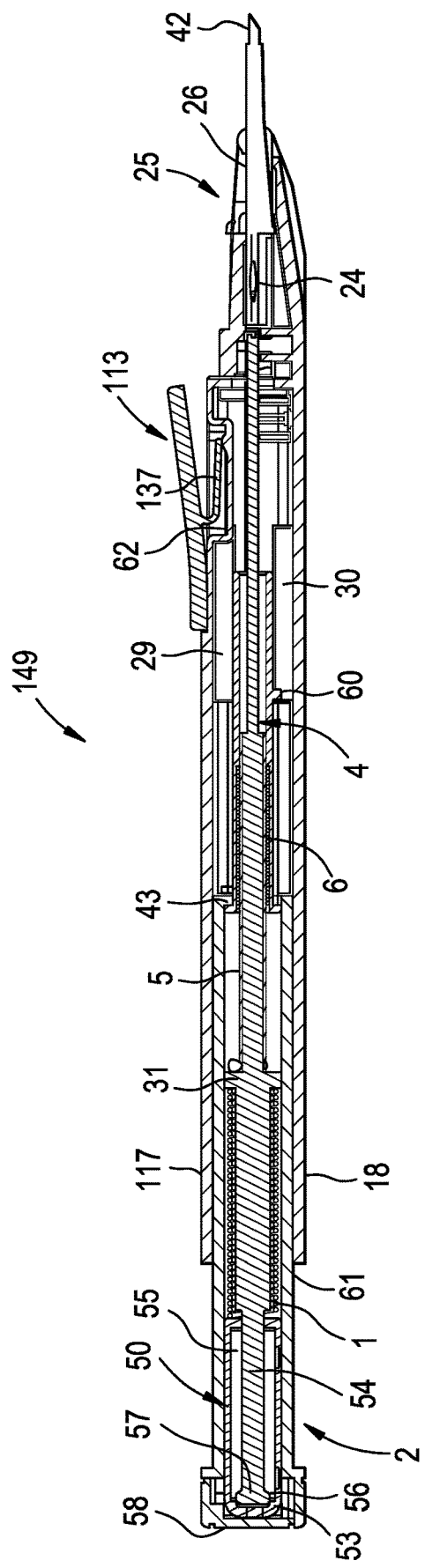
FIG. 17 is a cross-sectional view like FIGS. 2 and 12, but of an IOL delivery device which is in accordance with a third embodiment of the present invention.
Figure 18:
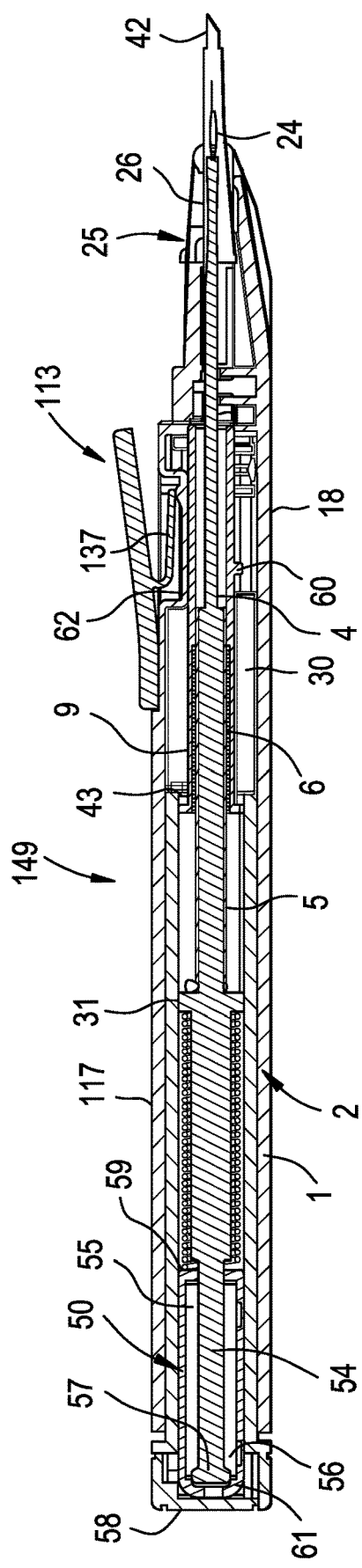
FIG. 18 is a is a view similar to FIG. 17, but shows the IOL delivery device after the plunger button of the device has been pressed in, placing the IOL in a staged condition prior to IOL deployment.
Figure 19:
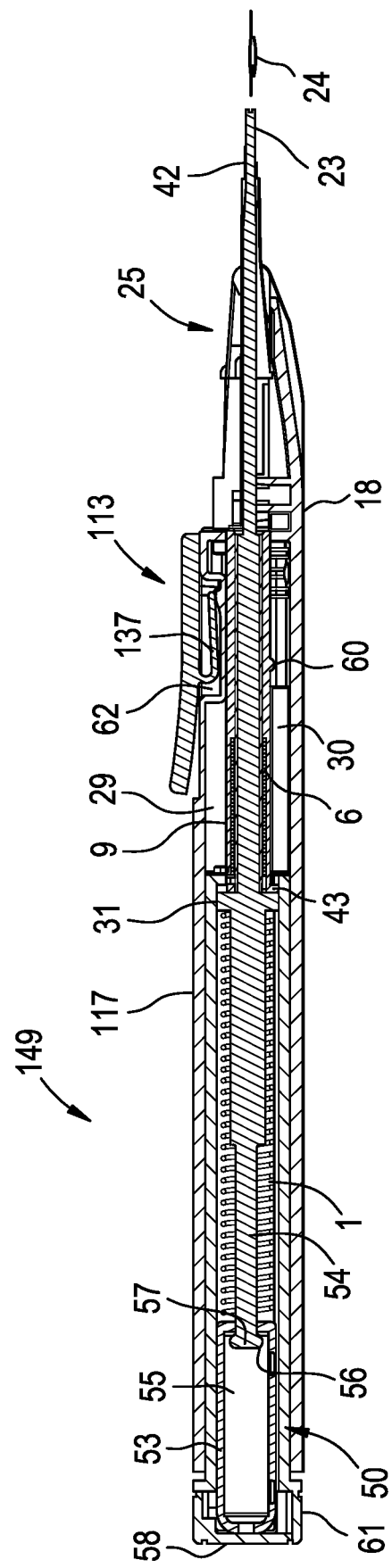
FIG. 19 is a view similar to FIG. 18, but shows a pivoting control button of the device in a fully depressed position and a plunger of the device in a fully extended position, following deployment of the IOL.
Figure 20:
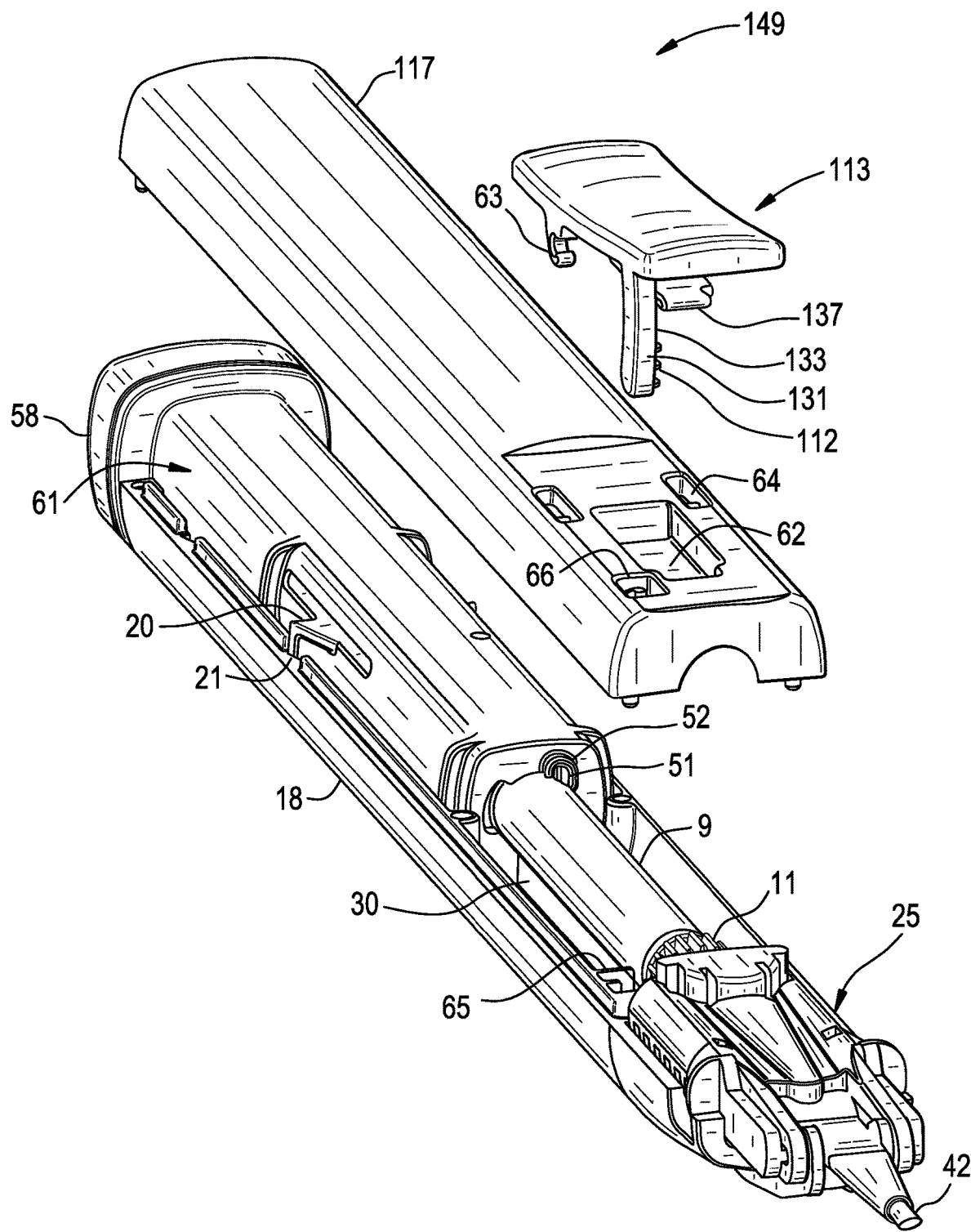
FIG. 20 is an internal view of the IOL delivery device shown in FIGS. 17-19, shown in the IOL staged position, and shown with a housing top and pivoting control button of the device exploded away, to provide a better view of inside the device and a better view of structural features of both the housing top and pivoting control button.

Specifically, FIG. 17 is a longitudinally sectioned side view of the improved IOL delivery device 149, shown in its delivered condition prior to use. FIG. 18 is a longitudinally sectioned side view of the improved IOL delivery device 149, shown with the plunger button 2 of the device 149 pressed in, placing the IOL 24 in a staged condition prior to IOL 24 deployment. FIG. 19 is a longitudinally sectioned side view of the improved IOL delivery device 149, showing a pivoting control actuator 113 of the device 149 in a fully depressed position, and showing the plunger 4 fully extended, following IOL 24 deployment. FIG. 20 is an internal view of the improved IOL delivery device 149, shown in the IOL staged position, and showing a housing top 17 and pivoting control actuator 113 exploded away, to provide a better view of inside the device 149, and a better view of structural features of both the housing top 17 and the pivoting control actuator 113.

The configuration of the third embodiment IOL delivery device 149 employs all previously described features relating to the IOL delivery device 100 shown in FIGS. 12-15, but also adds certain features. Specifically, compared to the IOL delivery device 49 described previously, the IOL delivery device 149 effectively replaces the linear operating, push down control button 13 of device 49 with a pivoting control actuator 113, which more closely mimics the natural finger motion of a hand, thereby making the device IOL delivery device 149 shown in FIGS. 17-20 more ergonomic to operate than the IOL delivery device 49 shown in FIGS. 12-15.

To facilitate substitution of the control button 13 with the pivoting control actuator 113, a different housing top 117 is employed, and the return spring of the IOL delivery device 49 is eliminated. As best shown in FIG. 20, the revised housing top 117 preferably includes a return spring pocket 62, a pair of button pivot sockets 64, and a gear rack passageway 66. Correspondingly, the pivoting control actuator 113 preferably includes pivot members 63, a depending leg 131 having a gear rack 133 thereon, and a return spring 137, all of which are preferably integral with the pivoting control actuator 113. Preferably, the pivot sockets 64 of the hosing top 117 are configured to locate and retain the pivot members 63 of the pivoting control actuator 113, the return spring pocket 62 of the housing top 117 is configured to receive the return spring 137, and gear rack passageway 66 provided in the housing top 117 is configured to receive the depending leg 131 of the pivoting control actuator 113 such that the depending leg 131 passes through the gear rack passageway 66 and the gear rack 133 on the depending leg 131 engages the pinion 11 (described previously) inside the device 149. Preferably, a gear rack guide 65 is provided in the device 149 for effectively backstopping the depending leg 131 of the pivoting control actuator 113 and provide support against deflection of the depending leg 131 whenever the gear rack 112 on the depending leg 131 is operationally engaged with the pinion 11.

When assembled together, the housing top 117 and the pivoting control actuator 113 combine to form a sub-assembly that is easier and. Therefore, less expensive to assemble, has fewer parts, and provides less frictional interference during use than the combination of the housing top 17 and control button of the device 49 shown in FIGS. 12-15, described previously, whose legs 33, 34 are located by, and wear against, corresponding pockets 35, 36. As described previously, the IOL delivery device 49 also requires a separate control spring 37, located within the housing bottom 18, to return the control button 13 to its home position, during use.

User interface with regard to the IOL delivery device 149 shown in FIGS. 17-20 is substantially the same as with the IOL delivery devices 100 and 49, described previously. However, the pivoting control actuator 113 of the IOL delivery device shown in FIGS. 17-20 provides an operator with a much larger bearing surface than offered by the control button 13 of the IOL delivery devices 100 and 49. This results in less force per unit of surface area upon the user's finger, which is more comfortable. The gentle rotation, or pivoting, of the pivoting control actuator 113 also mimics the natural finger motion of a hand, thereby making it more ergonomic to operate than a liner operating push button, such as the control button 13 which is provided on the IOL delivery devices 100 and 49, described previously. Additionally, because the length of the pivoting control actuator 113 can be shaped and configured to extend beyond the point where the gear rack 133 on the depending leg 131 contacts the pinion 11, the pivoting control actuator 113 offers users the mechanical advantage of a lever to reduce user input force required to operate the mechanism that controls movement of the plunger 4, and places the user's finger closer to the tip 42 for better control while implanting the IOL 24 within a patient's eye.

Assembly of the IOL delivery device 149 is consistent with that of the IOL delivery device 49 described previously, but without the use of the housing top 17 or installation of the return spring 37 and control button 33 into the housing bottom 18. In place of these components, the pivoting control actuator 113 is snapped in place relative to the housing top 117, and then the housing top 117 is simply installed directly onto the housing bottom 118.

Figure 21:
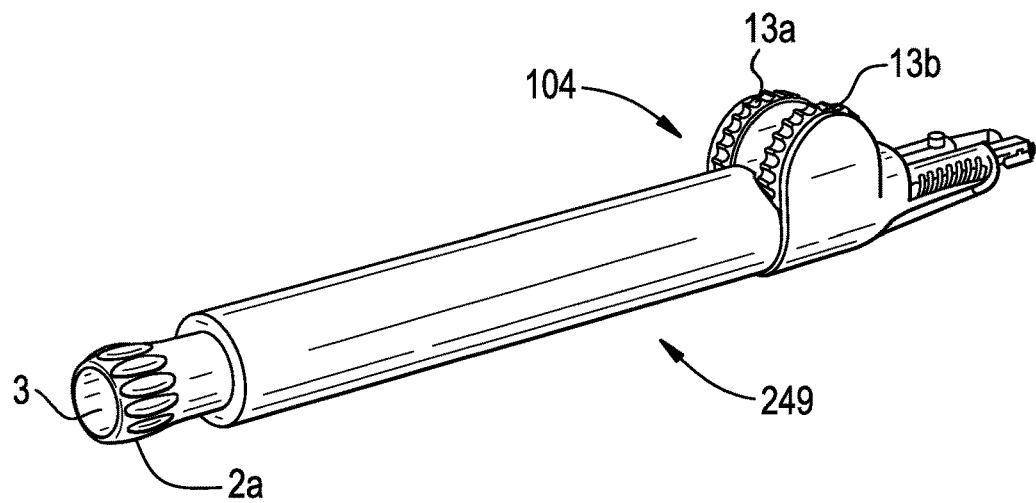
FIG. 21 is a perspective view of an IOL delivery device which is in accordance with still yet another embodiment of the present invention.
Figure 22:
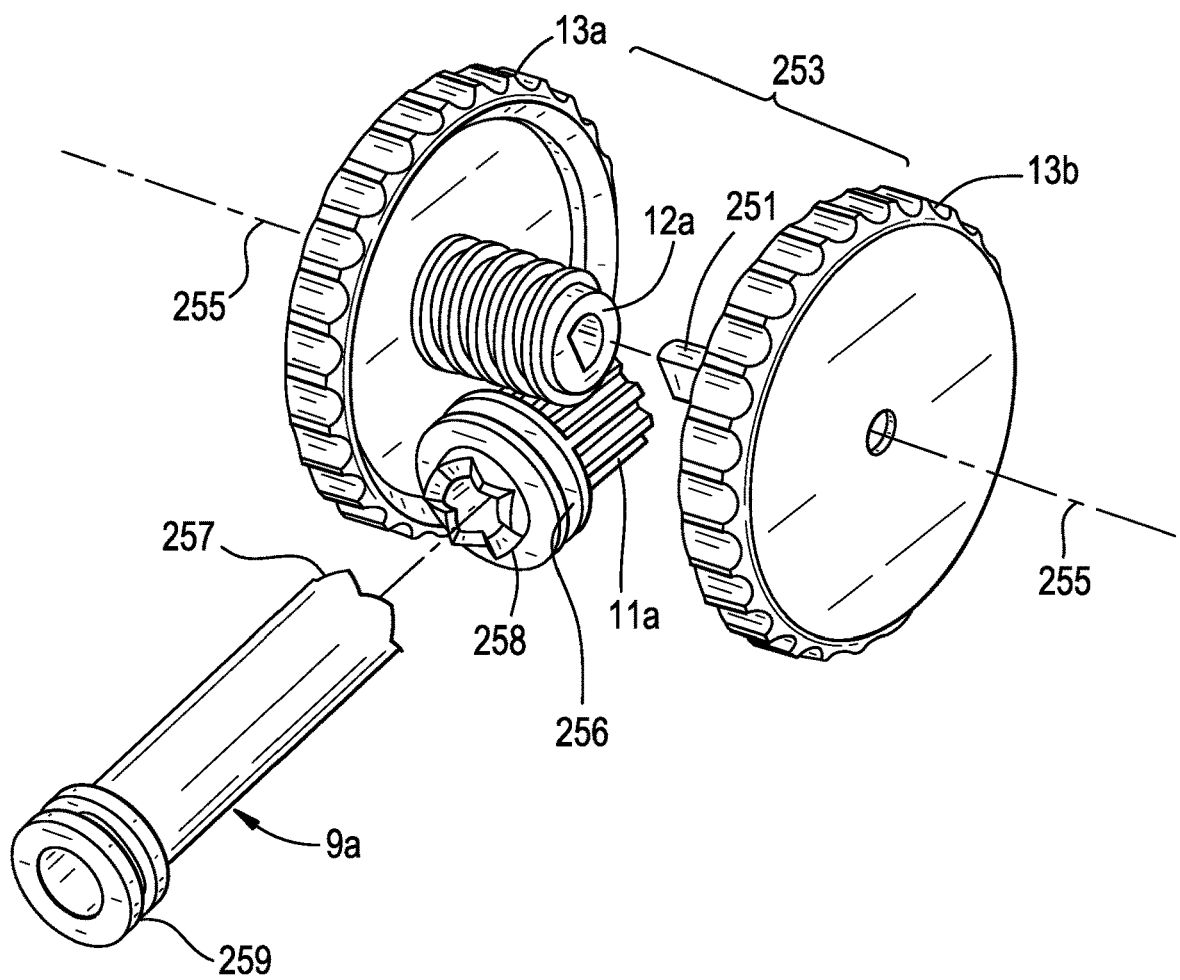
FIG. 22 is an exploded perspective view of a few of the components of the IOL delivery device shown in FIG. 21.

FIGS. 21 and 22 relate to yet a further improved IOL delivery device 249 which is in accordance with a fourth embodiment of the present invention. The IOL delivery device 249 is very similar to the IOL delivery device 100 described previously in terms of structure and operation, so only the differences will be explained in detail, and like reference numerals are used to identify like parts.

On the outside, the IOL delivery device 249 differs from the IOL delivery device 100 in that a differently configured micro movement actuator 104 is provided. On the inside, the IOL delivery device 249 differs from the IOL delivery device 100 in that a different type of engagement is provided between the micro movement actuator 104 and a rotating sleeve 9a on the inside of the device 249. Both of these differences will now be described in detail.

Like the IOL delivery device 100, the IOL delivery device 249 includes both a macro movement actuator 102 (such as a plunger button 2a, which is very similar to the plunger button 2 described previously in connection with IOL delivery device 100, but is just shaped differently at the end 3 which is meant to be engaged by a user) and a micro movement actuator 104, but the micro movement actuator 104 of the IOL delivery device 249 is preferably provided as being different than that of the IOL delivery device 100. As discussed above, the micro movement actuator of the IOL delivery device 100 is preferably provided such that successively pressing button 13 moves rack 12 and turns pinion 11 causing the sleeve 9 to rotate. In contrast, the IOL delivery device 249 is configured such that the micro movement actuator 104 is provided as comprising a pair of wheels 13a, 13b which are continuously pivotable to cause a sleeve 9a inside the device 249 to rotate. Like the sleeve 9 described previously in connection with the description of IOL delivery device 100, the sleeve 9a of IOL delivery device 249 is disposed inside the housing 16 (see FIG. 2, for example), forward of the plunger button 2a, journaled in a bearing provided in the housing 16, wherein the bearing is provided via bearing sections 43 provided on the plunger button halves 14, 15 which are straddled by thrust flanges 259 and bearing sections 44 provided on the housing halves 17, 18 (see FIG. 2, for example).

However, as shown in FIG. 22, instead of having a pinion 11 at its front end, preferably the rotating sleeve 9a of the IOL delivery device 249 has a gear 11a couplable to its front end which, like the pinion 11 of the rotating sleeve 9 of the IOL delivery device 100, functions to turn the rotating sleeve 9a. As described above, the IOL delivery device 100 provides that successively pressing button 13 moves rack 12 and turns pinion 11 causing the sleeve 9 to rotate. In contrast, it is the pivotable rotation resulting from the pressing and turning of one or both of the pivoting wheels 13a, 13b downward or forward which causes the sleeve 9a to rotate. This translation of rotation of the wheels 13a, 13b to rotation of the sleeve 9a occurs due to threaded engagement of the gear 11a with a worm gear 12a that is disposed between the pivoting wheels 13a, 13b.

As shown in FIG. 22, preferably one pivoting wheel 13a has the worm gear extending therefrom, while the other pivoting wheel 13b has a protrusion 251 or some other suitable structure which is configured to engage the other wheel 13a and form a pivoting wheel assembly 253 having two pivoting wheels 13a, 13b and a worm gear 12a disposed between the two pivoting wheels 13a, 13b. As such, pushing of either pivoting wheel 13a or 13b causes the entire assembly 253 to rotate about the axis 255 effectively defined by the worm gear 12a which preferably coincides with the central axes of both pivoting wheels 13a, 13b.

Like the IOL delivery device 100, the IOL delivery device 249 preferably lacks a non-Newtonian damper element in the plunger button 2a, and includes an unconstrained rotating spring clutch 6 (see FIGS. 2-4, for example), a rotating sleeve 9a with spring engagement pocket 8, and a gear 11 a which functions to turn the rotating sleeve 9a.

As described above, the IOL delivery device 100 shown in FIGS. 1-11 provides that successively pressing button 13 moves rack 12 and turns gear 11. The IOL delivery device 249 shown in FIGS. 21 and 22 is configured to effectively provide an evolved approach that differs slightly compared to the IOL delivery device 100 in terms of actuation detail. In this approach, the function of button 13 with rack 12 is replaced with a set of keyed together (preferably knurled) pivoting wheels 13a, 13b, in effect roller actuators, having an attached or integral worm gear 12a residing between them. When the pivoting wheels 13a, 13b are pressed downward or forward by the user's finger, the pivoting wheels 13a, 13b pivot on their center axes, thereby turning the attached worm gear 12a that is disposed between them. This worm gear 12a, in turn, drives a helical gear 11 a which is no longer integral to the new rotating sleeve 9a but instead supported and permanently retained in place and engaged with worm gear 12a, by a set of journaled bearing halves similar to journaled bearings 43 but provided on housing halves 17 and 18 that are straddled by thrust flanges 256. The new rotating sleeve 9a is still carried by bearings 43 of the plunger button halves 14 and 15. This new rotating sleeve 9a couples to gear 11a when plunger button 2 is advanced longitudinally thereby engaging the mating toothed features 257 and 258 provided on these respective parts.

This embodiment of the present invention effectively takes into account potentially conflicting requirements between lens folding and user control. Doctors want ultimate control of the delivery speed, but delivery speed must not exceed what the lens can accept without becoming damaged. The IOL delivery device 249 effectively meets these conflicting needs.

While specific embodiments of the invention have been shown and described, it is envisioned that those skilled in the art may devise various modifications without departing from the spirit and scope of the present invention.

What is claimed is:

1. An intraocular lens delivery device for retaining and delivering an intraocular lens, said intraocular lens delivery device comprising: a macro movement actuator which is configured to be actuated to move the intraocular lens into position in the device for the intraocular lens to be delivered; and a micro movement actuator comprising at least one pivotable member which is configured to be pivoted to deliver the intraocular lens, further comprising a rotating sleeve, wherein the rotating sleeve comprises a pinion which engages the micro movement actuator.

2. The intraocular lens delivery device as recited in claim 1, wherein the macro movement actuator comprises a plunger which is configured to be pushed to move the intraocular lens into position in the device for the intraocular lens to be delivered.

3. The intraocular lens delivery device as recited in claim 1, wherein the at least one pivotable member comprises a pair of pivotable members which are configured to be pushed to deliver the intraocular lens.

4. The intraocular lens delivery device as recited in claim 1, wherein the at least one pivotable member comprises at least one rotatable wheel.

5. The intraocular lens delivery device as recited in claim 1, further comprising a housing having an end and a top, wherein the macro movement actuator extends from the end of the housing, and the micro movement actuator is disposed on the side of the housing.

6. The intraocular lens delivery device as recited in claim 1, further comprising a plunger having a flange which provides a spring perch, a plunger button having an inside surface, and a drive spring disposed inside the plunger button, wherein the drive spring extends between the inside surface of the plunger button and the spring perch provided by the flange on the plunger.

7. The intraocular lens delivery device as recited in claim 1, further comprising a plunger, a plunger button having an inside surface, and at least one guideway on the inside surface of the plunger button configured to engage the plunger, and keep the plunger from rotating inside the intraocular lens delivery device.

8. The intraocular lens delivery device as recited in claim 7, further comprising a housing having at least one notch, wherein the plunger button has an external surface, further comprising at least one deflectable latch on the external surface of the plunger button which engages the at least one notch on the housing.

9. The intraocular lens delivery device as recited in claim 1, further comprising a revolving spring clutch inside the intraocular lens delivery device.

10. The intraocular lens delivery device as recited in claim 9, further comprising a wear sheath disposed radially inward of the revolving spring clutch, wherein the revolving spring clutch selectively constrains and releases the wear sheath.

11. The intraocular lens delivery device as recited in claim 10, wherein the rotating sleeve has a spring engagement pocket which receives a portion of the revolving spring clutch, and comprising a thrust shoulder for engaging a spring pawl at an end of the revolving spring clutch.

12. The intraocular lens delivery device as recited in claim 1, wherein the micro movement actuator comprises a worm gear which engages a gear inside the intraocular lens delivery device.

\* \* \* \* \*